(12) United States Patent
Svendsen et al.

(10) Patent No.: US 10,231,954 B2
(45) Date of Patent: Mar. 19, 2019

(54) NEURODEGENERATIVE THERAPIES

(71) Applicant: LYTIX BIOPHARMA AS, Tromso (NO)

(72) Inventors: John S. Svendsen, Kvaloysletta (NO); Wenche Stensen, Kvaloysletta (NO); Frederick A. Leeson, Tromso (NO)

(73) Assignee: LYTIX BIOPHARMA AS, Tromso (NO)

( * ) Notice: Subject to any disclaimer, the term of this patent is extended or adjusted under 35 U.S.C. 154(b) by 0 days.

(21) Appl. No.: 15/116,296

(22) PCT Filed: Feb. 4, 2015

(86) PCT No.: PCT/EP2015/052330
§ 371 (c)(1),
(2) Date: Aug. 3, 2016

(87) PCT Pub. No.: WO2015/118026
PCT Pub. Date: Aug. 13, 2015

(65) Prior Publication Data
US 2017/0007583 A1    Jan. 12, 2017

(30) Foreign Application Priority Data
Feb. 4, 2014 (GB) .................................. 1401886.5

(51) Int. Cl.
- *A61K 31/428* (2006.01)
- *A61K 31/4439* (2006.01)
- *C12N 9/99* (2006.01)

(52) U.S. Cl.
CPC ........ *A61K 31/428* (2013.01); *A61K 31/4439* (2013.01); *C12N 9/99* (2013.01)

(58) Field of Classification Search
CPC ............................ A61K 31/428; C07D 277/82
See application file for complete search history.

(56) References Cited

U.S. PATENT DOCUMENTS

| | | | |
|---|---|---|---|
| 6,140,330 A | 10/2000 | Mori et al. | |
| 7,091,227 B2 * | 8/2006 | Scott ................... | C07D 231/12 514/367 |
| 2002/0002161 A1 | 1/2002 | Ennis et al. | |
| 2004/0152747 A1 * | 8/2004 | Chen .................... | C07D 277/46 514/370 |
| 2005/0171026 A1 | 8/2005 | Hagiwara et al. | |
| 2006/0167029 A1 | 7/2006 | Matasi et al. | |
| 2006/0247253 A1 | 11/2006 | Leban et al. | |
| 2006/0276496 A1 | 12/2006 | Goldberg et al. | |
| 2009/0054410 A1 | 2/2009 | Griffioen et al. | |
| 2009/0325987 A1 | 12/2009 | Muthuppalniappan et al. | |
| 2010/0154192 A1 | 6/2010 | Takita et al. | |
| 2010/0160290 A1 | 6/2010 | Kobayashi et al. | |
| 2010/0267717 A1 * | 10/2010 | Leban ................. | C07D 263/48 514/234.5 |
| 2012/0095022 A1 | 4/2012 | Routier et al. | |
| 2012/0115903 A1 | 5/2012 | Frank et al. | |
| 2015/0210680 A1 | 7/2015 | Kobayashi et al. | |
| 2015/0352082 A1 * | 12/2015 | Martínez Gil ....... | A61K 31/428 514/367 |

FOREIGN PATENT DOCUMENTS

| | | |
|---|---|---|
| CA | 2628074 A1 | 5/2007 |
| EP | 1834954 A1 | 9/2007 |
| WO | 0152847 A1 | 7/2001 |
| WO | 01072752 A2 | 10/2001 |
| WO | 03093250 A2 | 11/2003 |

(Continued)

OTHER PUBLICATIONS

Salado et al., Journal of Medicinal Chemistry (published Mar. 4, 2014), 57(6), pp. 2755-2772.*
Thompson et al., Current Medicinal Chemistry, Oct. 2002, 9(19), pp. 1751-1762.*
Guttman et al., Canadian Medical Association Journal, Feb. 4, 2003, 168(3), pp. 293-301.*
Thomas et al., Human Molecular Genetics, 2007, vol. 16, Review Issue 2, pp. R183-R194.*
Ogawa, et al: "Development of a Novel Selective Inhibitor of the Down Syndrome-Related Kinase Dyrk1A", Nature Communications, Oct. 5, 2010, Article 86, pp. 1-9.
Xie, et al.: "Identification of Small-Molecule Inhibitors of the AB-ABAD Interaction", Bioorganic & Medicinal Chemistry Letters, 2006, vol. 16, pp. 4657-4660.

(Continued)

*Primary Examiner* — Laura L Stockton
(74) *Attorney, Agent, or Firm* — Fox Rothschild LLP

(57) ABSTRACT

The present invention provides a compound of formula (I) wherein: Y represents a C or N atom which may be substituted or form a cyclic group with R''' but may not be a quaternary C atom; R' is —$OR_1$, —$CONH_2$, —$CF_3$, F, —OH, —$NO_2$, —CN or —$OCOR_1$ in which $R_1$, is $C_{1-3}$ alkyl and each may be in the beta or gamma position; R" is $C_{1-3}$ alkyl or H; and R''' is H or a group consisting of 1-12 non-hydrogen atoms and may be linear, branched and/or incorporate one or more cyclic groups, cyclic groups may be aromatic and/or heterocyclic and 2 or more cyclic groups may be linked or fused and each may be substituted; or a salt, hydrate or solvate of a compound of formula (I) for use in the treatment or prevention of a neurodegenerative disorder by inhibiting formation of neurofibrillary (tau) tangles and/or by inhibiting Dyrk 1A. The invention further relates to non-therapeutic uses of these compounds.

7 Claims, No Drawings
Specification includes a Sequence Listing.

(56) References Cited

FOREIGN PATENT DOCUMENTS

| WO | 2004033439 A1 | 4/2004 |
|---|---|---|
| WO | 2004094375 A2 | 11/2004 |
| WO | 2005026137 A2 | 3/2005 |
| WO | 2005/037845 A1 | 4/2005 |
| WO | 2005037779 A2 | 4/2005 |
| WO | 2005040355 A2 | 5/2005 |
| WO | 2005053610 A2 | 6/2005 |
| WO | 2005099707 A1 | 10/2005 |
| WO | 2006002051 A1 | 1/2006 |
| WO | 2006006741 A1 | 1/2006 |
| WO | 2006018662 A2 | 2/2006 |
| WO | 2007042906 A1 | 4/2007 |
| WO | 2007104557 A2 | 9/2007 |
| WO | 2007104558 A1 | 9/2007 |
| WO | 2007118853 A1 | 10/2007 |
| WO | 2007137417 A1 | 12/2007 |
| WO | 2007146066 A2 | 12/2007 |
| WO | 2008014199 A2 | 1/2008 |
| WO | 2008051757 A1 | 5/2008 |
| WO | 2009060054 A1 | 5/2009 |
| WO | 2009061652 A1 | 5/2009 |
| WO | 2010000797 A1 | 1/2010 |
| WO | 2010010797 A1 | 1/2010 |
| WO | 2010066357 A1 | 6/2010 |
| WO | 2010077068 A2 | 7/2010 |
| WO | 2010078408 A1 | 7/2010 |
| WO | 2010096371 A2 | 8/2010 |
| WO | 2010103381 A1 | 9/2010 |
| WO | 2011097600 A1 | 8/2011 |
| WO | 2011130595 A2 | 10/2011 |
| WO | 2012059442 A2 | 5/2012 |
| WO | WO-2014/114825 A1 * | 7/2014 |

OTHER PUBLICATIONS

Himmelstein, et al: "Tau as a Therapeutic Target in Neurodegenerative Disease", Pharmacol. Ther. Oct. 2012, vol. 136, No. 1, pp. 8-22.
Kim, et al: "Putative Therapeutic Agents for the Learning and Memory Deficits of People with Down Syndrome", Bioorganic & Medicinal Chemistry Letters, 2006, No. 16, pp. 3772-3776.
Ryoo, et al: "DYRK1A-Mediated Hyperphosphorylation of Tau A Functional Link Between Down Syndrome and Alzheimer Disease", Journal of Biological Chemistry, Nov. 30, 2007, vol. 282, No. 48, pp. 34850-34857.
Wu, et al: "Dibenzothiazoles as Novel Amyloid-Imaging Agents", Bioorganic & Medicinal Chemistry, 2007, vol. 15, pp. 2789-2796.
Guedj, et al: "Green Tea Polyphenols Rescue of Brain Defects Induced by Overexpression of DYRK1A", PLoS One, Feb. 2009, vol. 4, Issue 2, pp. 1-8.
Savage, et al.: "Advances in the Development of Kinase Inhibitor Therapeutics for Alzheimer's Disease", Drug Development Research, 2009, vol. 70, pp. 125-144.
Brunden, et al: "Advances in Tau-Focused Drug Discovery for Alzheiimer's Disease and Related Tauopathies", Nature Reviews, Oct. 2009, vol. 8, pp. 783-793.
Yin, et al: "Benzothiazoles as Rho-Associated Kinase (ROCK-II) Inhibitors", Biiorganic & Medicinal Chemistry Letters, 2009, vol. 19, pp. 6686-6690.
Swahn, et al: "Synthesis and Evlauation of 2-pyridylbenzothiazole, 2-pyridylbenzoxazole and 2-pyridylbenzofuran Derivatives as 11C-PET Imaging Agents for B-Amyloid Plaques", Bioorganic & Medicinal Chemistry Letters, 2010, vol. 20, pp. 1976-1980.
Martin Citron: "Alzheimer's Disease: Strategies for Disease Modification", Nature Reviews, May 2010, vol. 9, pp. 387-398.
Wegiel, et al: "The Role of DYRK1A in Neurodegenerative Diseases", FEBS Journal, 2011, vol. 278, pp. 236-245.
Medeiros, et al: "The Role of Tau in Alzheimer's Disease and Related Disorders", CNS Neuroscience & Therapeutics, 2011, vol. 17, pp. 514-524.
Becker, et al: "Activation, Regulation, and Inhibition of DYRK1A", FEBS Journal, 2011, vol. 278, pp. 246-256.
Frost, et al: "B-Carboline Compounds, Including Harmine, Inhibit DYRK1A and Tau Phosphorylation at Multiple Alzheimer's Disease-Related Sites", PLoS One, May 2011, vol. 6, Isue 5, pp. 1-9.
Rosenthal, et al: "Potent and Selective Small Molecule Inhibitors of Specific Isoforms of Cdc-2-like Kinases (Clk) and Dual Specificity Tyrosine-Phosphorylation-Regulated Kinases (Dyrk)", Bioorganic & Medicinal Chemistry Letters, 2011, vol. 21, pp. 3152-3158.
Debdab, et al: "Leucettines, a Class of Potent Inhibitors of cdc2-Like Kiinases and Dual Specificity, Tyrosine Phosphorylation Regulated Kinases Derived from the Marine Sponge Leucettamine B: Modulation of Alternative Pre-RNA Splicing", Journal of Medicinal Chemistry, 2011, vol. 54, pp. 4172-4186.
Wang, et al: "Discovery of Potent Small Molecule Inhibitors of DYRK1A by Structure-Based Virtual Screening and Bioassay", Bioorganic & Medicinal Chemistry Letters, 2012, vol. 22, pp. 168-171.
Neagoie, et al: "Synthesis of Chromeno[3,4-b]indoles as Lamellarin D Analogues: A Novel DYRK1A Inhibitor Class", European Journal of Medicinal Chemistry, 2012, vol. 49, pp. 379-396.
Smith, et al: "Recent Advances in the Design, Synthesis, and Biological Evaluation of Selective DYRK1A Inhibitors: A New Avenue for a Disease Modifying Treatment of Alzheimier's?", ACS Chemical Neuroscience, 2012, vol. 3, pp. 857-872.
Coulibaly et al: "Synthesis of N,N'-bis(5-arylidene-4-oxo-3,5-dihydro-4H-imidazol-2-yl)diamines Bearing Various Linkers and Biological Evaluation as Potential Inhibitors of Kinases", European Journal of Medicinal Chemistry, 2012, vol. 58, pp. 581-590.
Loidreau, et al: "Synthesis and Biological Evaluation of N-aryl-7-methoxybenzol[b]furo[3,2-d] pyrimidin-4-amines and their N-arylbenzo[b]thieno[3,2-d]pyrimidin-4-amine Analogues as Dual Inhibitors of CLK1 and DYRK1A Kinases", European Journal of Medicinal Chemistry, 2013, vol. 59, pp. 283-295.
Bharate, et al: "QSAR and Pharmacophore Study of Dyrk1A Inhibitory Meridianin Analogs as Potential Agents for Treatment of Neurodegenerative Diseases", Medicinal Chemistry, 2013, vol. 9, 152-161.
Luan, et al: "TOPS-MODE Model of Multiplexing Neuroprotective Effects of Drugs and Experimental-Theoretic Study of New 1,3-Rasagiline Derivatives Potentially Useful in Neurodegenerative Diseases", Bioorganic & Medicinal Chemistry, 2013, vol. 21, pp. 1870-1879.
Khan, et al: "Ligand Based Pharmacophore Model Development for the Identification of Novel Antiepileptic Compound", Epilepsy Research, 2012, vol. 98, pp. 62-71.
Siddiqui, et al: "Synthesis and Anticonvulsant Activity of Sulfonamide Derivatives-Hydrophobic Domain", Bioorganic & Medicinal Chemistry Letters, 2007, vol. 17, pp. 255-259.
Lo Monte, et al: "Synthesis and Biological Evaluation of Glycogen Synthase Kinase 3 (GSK-3) Inhibitors: An Fast and Atom Efficient Access to 1-aryl-3-benzylureas", Bioorganic & Medicinal Chemistry Letters, 2011, vol. 21, pp. 5610-5615.
Kim, et al: "New Serotonin 5-HT6 Ligands from Common Feature Pharmacophore Hypotheses", J. Chem. Inf. Model, 2008, vol. 48, pp. 197-206.
Giraud, et al: Synthesis, Protein Kinase Inhibitory Potencies, and in Vitro Antiproliferative Activities of Meridianin Derivatives, Journal of Medicinal Chemistry, 2011, vol. 54, pp. 4474-4489.

* cited by examiner

NEURODEGENERATIVE THERAPIES

This application is the U.S. National Phase of International Patent Application Serial No. PCT/EP 2015/052330, filed Feb. 4, 2015, which claims priority to United Kingdom Patent Application No. 1401886.5, filed on Feb. 4, 2014.

The present invention relates to the field of neurodegenerative disorders, in particular to Alzheimer's disease (AD).

AD is the most common form of dementia and no treatment exists which can stop, let alone reverse, progression of the disease. The memory and other mental health implications of AD are well known but the disease is also a killer; the average life expectancy after diagnosis is about 7 years as bodily functions are gradually lost. This is a common degenerative condition, generally affecting people over 65, and it is recognised as placing a significant burden on careers, health services and society in general as life expectancy continues to rise and the numbers of people affected by AD increases.

AD is characterised by loss of neurons and synapses in the cerebral cortex and some subcortical regions. Amyloid plaques and neurofibrillary tangles are observed in the brains of those with AD.

Amyloid plaques form on the outside of neurones and are made up of peptides of 39-43 amino acids called beta-amyloid ($A_\beta$), these are fragments of amyloid precursor protein, a trans-membrane protein that penetrates the neuron's membrane and is critical to neuron growth, survival and repair.

Neurofibrillary tangles are aggregates of the microtubule-associated protein tau which have become hyperphosphorylated and accumulated in the neurons. In healthy neurones, tau serves to stabilise the microtubules of the neuronal cytoskeleton. Certain conditions are characterised by an increase in these tau tangles and this group of conditions are referred to as tauopathies. Tauopathies include Parkinson's disease, Pick's disease and progressive supernuclear palsy, as well as AD. While an increase in amyloid plaques may be seen decades before the onset of symptoms of AD, the symptoms of AD are often observed just after a noticeable increase in tau protein is seen.

While it is generally accepted that these two proteins have a role in AD, the pathological mechanism and the causal events are not known. It had been postulated that the formation of amyloid plaques caused AD but therapies which successfully reduced plaque formation did not give significant improvement in symptoms such as dementia.

Current medication for AD shows limited benefit. Acetylcholinesterase inhibitors such as tacrine and donepezil are used to decrease the rate at which acetylcholine (ACha) is broken down in the brain, in order to counteract the reduction in cholinergic neuron activity which is associated with AD. These therapies have shown some benefit, at least in mild to moderate AD. The NMDA receptor antagonist memantine has been shown to have very modest efficacy in the treatment of moderate to severe AD.

There is undoubtedly an urgent need for further therapeutic options in the treatment of AD and other neurodegenerative conditions, whether to slow or halt disease progression, improve symptoms or delay onset; the tools available to the clinician at present are completely inadequate.

The present inventors have developed compounds which act as inhibitors of Dyrk1A (dual-specificity tyrosine-(Y)-phosphorylation-regulated kinase 1A), a kinase thought to be important in neonates and in the early stages of life. Dyrk1A is a kinase whose over-activity has recently been implicated in the pathogenesis of AD and other tauopathies.

The Dyrk1A gene is copied in triplicate in patients that have Down Syndrome (DS), who are themselves more likely to develop AD; between 50 and 70% of DS patients develop dementia by age 60 and nearly all DS patients have amyloid plaques and neurofibrillary tangles above the age of 30. Dyrk1A is thought to play a role in the development of AD, both by increasing amyloid plaque formation and increasing intracellular tau protein tangles. Studies have identified Dyrk1A as the priming kinase of multiple phosphorylation of the tau protein and studies of the brains of patients with AD showed increased expression of Dyrk1A in neurons affected by tau tangles.

Ogawa et al. in Nature Communications, 5 Oct. 2010 (1) Article 86 describe a Dyrk1A inhibitor called INDY, a benzothiazoylidene. INDY binds at the ATP binding cleft. INDY is not well able to cross cell membranes and has the complication that it must be administered as a prodrug. Harmine is a potent inhibitor of Dyrk1A but is hallucinogenic.

Thus there is a need for alternative and/or improved inhibitors of Dyrk1A. In particular for highly selective kinase inhibitors so that off-target effects on other kinases are reduced. It is also necessary for the compounds to pass the blood brain barrier. The present inventors have identified a new class of Dyrk1A inhibitor which possess some or all of these advantageous features.

According to one aspect, the present invention provides a compound of formula (I)

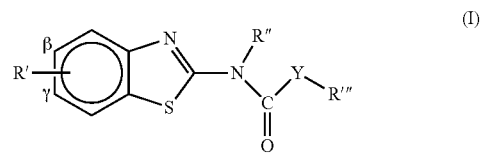

wherein:
Y represents a C or N atom which may be substituted or form a cyclic group with R''' but may not be a quaternary C atom;
R' is —$OR_1$, —$CONH_2$, —$CF_3$, F, —OH, —$NO_2$, —CN or —$OCOR_1$ in which $R_1$ is $C_{1-3}$ alkyl and each may be in the beta or gamma position;
R" is $C_{1-3}$ alkyl or H; and
R''' is H or a group consisting of 1-12 non-hydrogen atoms and may be linear, branched and/or incorporate one or more cyclic groups, cyclic groups may be aromatic and/or heterocyclic and 2 or more cyclic groups may be linked or fused and each may be substituted;
or a salt, hydrate or solvate of a compound of formula (I) for use in the treatment or prevention of a neurodegenerative disorder by inhibiting formation of neurofibrillary (tau) tangles.

The compounds of formula (I) are Dyrk1A inhibitors and preferably can cross the blood brain barrier. In a further aspect the present invention provides a compound of formula (I) as defined herein, or a salt, hydrate or solvate of a compound of formula (I), for use in the treatment or prevention of a neurodegenerative disorder by inhibiting Dyrk1A.

A quaternary C atom is one bonded to 4 other C atoms.

In a further aspect, the present invention provides a method of treating or preventing a neurodegenerative disease in a subject comprising administering a therapeutically effective amount of a compound of formula (I)

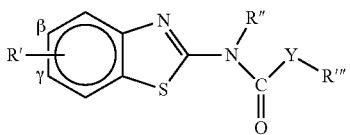

(I)

wherein:
Y represents a C or N atom which may be substituted or form a cyclic group with R''' but may not be a quaternary C atom;
R' is —OR$_1$, —CONH$_2$, —CF$_3$, F, —OH, —NO$_2$, —CN or —OCOR$_1$ in which R$_1$ is C$_{1-3}$ alkyl and each may be in the beta or gamma position;
R'' is C$_{1-3}$ alkyl or H; and
R''' is H or a group consisting of 1-12 non-hydrogen atoms and may be linear, branched and/or incorporate one or more cyclic groups, cyclic groups may be aromatic and/or heterocyclic and 2 or more cyclic groups may be linked or fused and each may be substituted;
or a salt, hydrate or solvate of a compound of formula (I) to said subject, with the proviso that the compound of formula (I) is not:
(i) one of the following compounds of formula (II)

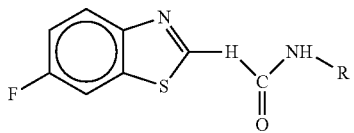

(II)

in which R is benzyl substituted as follows:

| Compound | Benzyl substituent |
|---|---|
| (a) | 4-OH-5-COOH |
| (b) | 2-OH |
| (c) | 4-OH-5-COOCH$_3$ |
| (d) | 2-I-4-COOCH$_3$ | or (e) R is pyridyl, or
(ii) selected from
(f) N-(6-cyano-2-benzothiazolyl)-N-[(4-methoxyphenyl)methyl]-urea
(g) ethyl 2-(3-(6-fluorobenzo[d]thiazole-2-yl)ureido)acetate
(h) ethyl 2-(3-(6-methoxybenzo[d]thiazole-2-yl)ureido)acetate
(i) potassium 2-(3-(6-methoxybenzo[d]thiazole-2-yl)ureido)acetate
(j) 2-(3-(6-methoxybenzo[d]thiazole-2-yl)ureido)acetic acid
(k) N-(2,6-dimethylphenyl)-N-(6-fluoro-2-benzothiazolyl)urea
(l) benzeneacetamide, 3,5-difluoro-N-[(1S)-1-[[(6-methoxy-2-benzothiazolyl)amino]carbonyl]propyl].

A therapeutically effective amount is preferably one which is able to inhibit formation of neurofibrillary (tau) tangles (and thereby treat or prevent a neurodegenerative disorder). A therapeutically effective amount is preferably one which inhibits Dyrk1A (and thereby treats or prevents a neurodegenerative disorder).
Preferably the compounds of formula (I) for use according to, and in the methods of, the present invention do not include the following compounds:

(m) 2-(3,5-dimethylphenoxy)-N-(6-nitrobenzothiazol-2-yl)acetamide
(n) 1-(6-fluorobenzothiazol-2-yl)-3-(4-fluorophenyl)urea
(o) 1-(4-fluorophenyl)-3-(6-methoxybenzothiazol-2-yl) urea
(p) 4-[3-(6-fluorobenzothiazol-2-yl)ureido]benzoic acid ethyl ester
(q) benzeneacetamide, α-ethyl-N-(6-methoxy-2-benzothiazolyl)

Y is preferably carbon and preferably forms a cyclic group with R''', preferably an aromatic cyclic group. If Y forms a cyclic group with R''' then together the moiety —YR''' consists of no more than 13 non-hydrogen atoms. If Y is substituted, it is preferably by a C$_{1-3}$ alkyl group but in other preferred embodiments it is unsubstituted. If the Y atom is unsubstituted and not part of a cyclic group with R''', then Y is —CH$_2$— or —NH—.
R'' is preferably H or methyl, most preferably H.
R' is preferably attached to the 6 carbon atom unless it is —CF$_3$, —CONH$_2$, —NO$_2$ or —CN, in which case it is preferably attached to the γ carbon atom. —CF$_3$, —NO$_2$ and —CN are particularly preferred in the γ position. Preferably R' is not F.
R$_1$ is preferably methyl and thus —OCH$_3$ is a preferred R' moiety, if R' is —OCH$_3$ it is preferably attached to the β carbon atom.
R''' may, in certain preferred embodiments, be hydrogen and in this case YR''' together are preferably —NH$_2$ or —CH$_3$, most preferably CH$_3$.
In a further preferred embodiment R''' is C$_{1-5}$ alkyl, which may be linear or branched, or a derivative thereof which may optionally be substituted, e.g. by oxygen, nitrogen or a halogen. Preferred alkyl derivatives are those in which one of the carbon atoms is replaced by a nitrogen or oxygen atom. Thus, for example, R''' may be —CONH$_2$, —CH$_2$COCH$_3$, —CH$_2$CHNH$_2$CH$_3$, —NHCOCH$_3$, —CH$_2$CH$_3$, —CH$_2$CH$_2$CH$_3$, —COCH$_3$, —COCH$_2$CH$_3$, —CONHCH$_3$.
In further preferred embodiments R''' is an amino acylated amino acid or an acylated dipeptide. The acyl group is preferably acetyl. The amino acid(s) are preferably genetically encoded amino acids, more preferably selected from alanine, phenylalanine, tyrosine, proline or serine.
Alternatively, R''' or YR''' together may contain 1-3, preferably 1 or 2 cyclic groups, most preferably 1 cyclic group. For example, R''' or YR''' together may consist of one cyclic group of 3 to 7 ring atoms, preferably 3, 5 or 6 ring atoms, where at most 3 ring atoms are non-carbon atoms. Preferred non-carbon atoms are nitrogen, oxygen and sulphur, more preferably nitrogen and oxygen, most preferably nitrogen. The cyclic group may or may not be aromatic, but an aromatic ring is preferred.
The cyclic group is optionally substituted with one or more substituents containing a total of up to 8 non-hydrogen atoms. The substituents may be small (e.g. C$_{1-3}$) alkyl groups including cyclopropyl, but are preferably polar in nature. Examples of suitable substituents are presented in Table A below.
In alternative embodiments, R''' or YR''' together may contain two fused cyclic groups, for example two fused five membered rings, one five membered ring fused to a six membered ring or two fused six membered rings. The fused rings together may contain 0-5 non-carbon atoms (e.g. 1-3 non-carbon atoms), preferably nitrogen, oxygen or sulphur, more preferably nitrogen or oxygen, most preferably nitrogen. Neither, either or both, preferably both, of the fused rings may be aromatic.

One or more of the fused cyclic groups are optionally substituted with one or more substituents containing a total of up to 5 non-hydrogen atoms. The substituents may be small (e.g. $C_{1-3}$) alkyl groups, including cyclopropyl, but are preferably polar in nature. Examples of suitable substituents are presented in Table A below.

In alternative embodiments, R''' or YR''' together may contain two linked cyclic groups. The link may be direct forming a biaryl system or through a linking atom, usually carbon, nitrogen or oxygen. The linked rings together may contain 0-5 non-carbon atoms (e.g. 1-3 non-carbon atoms), preferably nitrogen, oxygen or sulphur, more preferably nitrogen or oxygen, most preferably nitrogen. Neither, either or both, preferably both, of the linked cyclic groups may be aromatic.

One or more of the linked cyclic groups are optionally substituted with one or more substituents containing up to 3 non-hydrogen atoms. The substituents may be small alkyl groups (e.g. $C_{1-3}$), including cyclopropyl, but are preferably polar in nature. Examples of suitable substituents are presented in Table A below.

TABLE A

Preferred substituents to the cyclic group(s) of —R''' or —YR''', ordered by the number of non-hydrogen atoms:

| No. of heavy atoms | Examples of suitable substituents |
|---|---|
| 1 | Methyl, halogen (F, Cl, Br), hydroxyl, amino and sulfhydryl |
| 2 | Ethyl, ethenyl (vinyl), ethynyl, methoxy, methylamino, methylsulfide, cyano and formyl |
| 3 | Propyl, isopropyl, cyclopropyl, methylsulfoxy, acetyl, nitro, dimethylamino, $CH_2CH_2OH$, $CH_2CH_2NH_2$, carboxylate, carboxamide |
| 4 | —$OCH_2CH_2OH$, —$NHCH_2CH_2OH$, —$OCH_2CH_2NH_2$, —$NHCH_2CH_2NH_2$, methylcarboxylate, N-methylcarboxamide, trifluoromethyl, methylsulfonyl, sulphonamide sulfonic acid |
| 5 | Methylsulfonylamido, trifluoromethoxy, cyclopropylmethoxy, N,N-dimethylcarboxamido |
| 6 | piperidyl, morpholinyl, —C=$ONHCH_2CH_2NH_2$, —C=$ONHCH_2CH_2OH$, C=$OOCH_2CH_2OH$ |
| 7 | $N(CH_2CH_2NH_2)_2$, $N(CH_2CH_2OH)_2$, methylpiperidyl |

Preferred linking groups include —$CH_2$—, —NR—, —O— and —S—, wherein R is H or $C_{1-2}$ alkyl.

If R''' or YR''' together contain two or more cyclic groups these may be the same or different and if they are substituted, the substituents may be the same or different.

If R''' or YR''' together comprise two or more aromatic groups, then preferably no more than one of these groups is carbocyclic.

Suitable cyclic groups for R''' or YR''' together include cyclohexyl, phenyl, pyridine, pyrimidine, pyrazole, imidazole, thiazole, oxazole, diazolone, morpholine and piperidine.

Preferred substituents of the cyclic group(s) of R''' (or YR''') include: —OH, —OR, —NRR, —C=O—OR, —C=O—NRR, —$SO_2$—NRR, —NR—$SO_2R$, —$SO_2R$, —NR—C=OR and a halogen (e.g. F or Cl), wherein each R (which may be the same or different) is H or $C_{1-3}$ alkyl, preferred substituents are $C_{1-3}$ alkyl or a derivative thereof which may itself be substituted (e.g. by oxygen, —$CH_3$, $NH_2$ or a halogen such as F).

In preferred embodiments, YR''' together form a single cyclic group, preferably aromatic and preferably 6 membered, most preferably, pyrimidinyl, pyridyl or phenyl; the cyclic group is optionally and preferably substituted, e.g. by $NH_2$ or a $C_{1-3}$ alkyl or derivative thereof which may itself be substituted e.g. by oxygen, nitrogen or a halogen. Preferred alkyl derivatives are those in which one of the carbon atoms is replaced by a nitrogen or oxygen atom. The substituent of the cyclic group may preferably be selected from the group comprising —$CONH_2$, —$CH_2COCH_3$, —$CH_2CHNH_2CH_3$, —$NHCOCH_3$, —$CH_2CH_3$, —$CH_2CH_2CH_3$, —$OCH_3$, —$COCH_3$, —$COCH_2CH_3$ and —$CONHCH_3$.

Pharmaceutically acceptable salts, hydrates and solvates are well known in the art.

Neurodegenerative disorders according to the present invention include Alzheimer's disease, Parkinson's disease, Pick's disease, progressive supranuclear palsy, corticobasal degeneration and agyrophilic grain disease. In particular the present invention concerns the treatment or prevention of Alzheimer's disease, more particularly the treatment or prevention of Alzheimer's disease in patients with Down Syndrome. Tauopathies are a particular target for treatment according to the present invention.

Treatment includes an improvement in one or more of the symptoms of the disorder or a delay in onset of one or more symptoms as assessed by a clinician, optionally together with patient feedback. Symptoms of AD include memory loss, confusion, mood and personality changes, hallucinations, delusions and paranoia, problems with communication, weight loss, seizures, skin infections, difficulty in swallowing and lack of control of bowel and bladder.

Treatment includes slowing or halting disease progression and thus treatment may not result in significant observable benefits unless a comparison is made with expected (untreated) progression of the disorder. Likewise, treatment may be beneficial if an anticipated symptom is delayed in its appearance.

The subject will typically have been identified as in need of treatment. This may be determined based on assessment of cognitive performance or any other measure which leads to a diagnosis that the patient has a neurodegenerative disorder or is at risk of developing such a disorder. In the case of AD this determination may be achieved through microscopic histological or other investigations to observe the formation of amyloid plaques and/or neurofibrillary tangles.

Prevention of a neurodegenerative disorder may include prevention for a period of time, in other words delayed onset. Suitable patients for prevention include those with DS, in particular, DS patients over the age of 20 or 30. Generally, if a patient has been shown to have one or more markers of a neurodegenerative disorder but no symptoms as yet, such a patient is considered to be "treated" in accordance with the present invention. "Prevention" assumes the patient has neither symptoms nor confirmed clinical markers of disease.

The present invention typically involves inhibition of the formation of neurofibrillary tangles. Without wishing to be bound by theory, this is believed to be key to the clinical success of the present invention and at least part of the mechanism by which the disclosed Dyrk1A inhibitors are effective against neurodegenerative disorders. These (tau) tangles can be assessed by any convenient method known in the art, for example using a microscope to observe the aggregates of the tau protein, a suitable method is described by Armstrong in Folia Neuropathol. 2008; 46 (1): 26-31.

Inhibition may be observed on treatment through a reduction in the size of the tangles or in the extent of their distribution. Their formation is "inhibited" even if the amount observed has not decreased on treatment, if the amount would have been expected to increase without treatment. Of course, such examinations of a patient may not be possible during a treatment regimen, but suitable studies can easily be performed to select a compound from within the definition of compounds of formula (I).

Alternatively viewed, the compounds described herein treat or prevent neurodegenerative disorders through inhibition of Dyrk1A. A method to measure inhibition of Dyrk1A is described in the Examples hereto. A suitable assay could be performed using ADP-Glo™ kinase assay of Promega. Compounds of the invention preferably can achieve at least 30, more preferably at least 50 or 60, most preferably at least 70 or 80% inhibition of Dyrk1A in such assays.

In a further aspect, the present invention provides a method of inhibiting Dyrk1A and/or a reaction catalysed by Dyrk1A, the method comprising contacting said kinase with a compound of formula (I) as defined herein or a salt, hydrate or solvate of a compound of formula (I). Such methods may be in vivo or ex vivo, e.g. in vitro.

In a further aspect, the present invention provides the use of a compound of formula (I) or a salt, hydrate or solvate of a compound of formula (I) in the manufacture of a medicament for the treatment of a neurodegenerative disorder.

Animals which may be treated include domestic animals, in particular cats and dogs and livestock animals such as pigs, cows, sheep or goats as well as horses. Laboratory animals, mice, rabbits etc. may also be treated. Treatment of humans is nevertheless preferred.

Methods for the synthesis of compounds of the invention are described in the Examples hereto, non-exemplified compounds can be prepared by methods which are analogous to the schemes and protocols described herein.

Methods of synthesising compounds of the invention, in particular methods described in the Examples, constitute a further aspect of the present invention.

All novel compounds, defined generically by the formulae herein or individual compounds recited, in particular in the Examples, constitute a further aspect of the present invention.

The compositions according to the invention may be presented, for example, in a form suitable for oral, nasal, parenteral, intravenal, topical or rectal administration.

The active compounds defined herein may be presented in the conventional pharmacological forms of administration, such as tablets, coated tablets, nasal sprays, inhalers, solutions, emulsions, liposomes, powders, capsules or sustained release forms. As used herein, the term "pharmaceutical" includes veterinary applications of the products of the invention.

Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays administration may be formulated similarly in aqueous solution and packed into spray containers either with an aerosol propellant or provided with means for manual compression.

Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Tablets for oral administration are preferred.

Pharmaceutical compositions comprising a compound of formula (I) may additionally comprise further active ingredients, including, for example, other active agents for the treatment or prevention of a neurogenerative disorder. Likewise the medical uses and methods of treatment may additionally comprise further active ingredients, including, for example, other active agents for the treatment or prevention of a neurogenerative disorder, e.g AD.

In employing such compositions systemically (intra-muscular, intravenous, intraperitoneal), the active molecule is generally present in an amount to achieve a serum level of the active molecule of at least about 1-10 micromolar Such serum levels may be achieved by incorporating the bioactive molecule in a composition to be administered systemically at a dose of from 50 mg-250 mg.

It is appreciated that appropriate dosages will vary from patient to patient dependent on age, sex, previous treatments, severity of symptoms presented etc.

The above description describes numerous features of the present invention and in most cases preferred embodiments of each feature are described. It will be appreciated that each preferred embodiment of a given feature may provide a molecule, use, method etc. of the invention which is preferred, both when combined with the other features of the invention in their most general form and when combined with preferred embodiments of other features. The effect of selecting multiple preferred embodiments may be additive or synergistic. Thus all such combinations are contemplated unless the technical context obviously makes them mutually exclusive or contradictory. In general each feature and preferred embodiments of it are independent of the other features and hence combinations of preferred embodiments may be presented to describe sub-sets of the most general definitions without providing the skilled reader with any new concepts or information as such.

The invention will now be further described with reference to the following non-limiting Examples. Not all of the compounds synthesised and tested are within the scope of the present invention, some are provided for comparative purposes and highlight the efficacy of the molecules of the invention.

EXAMPLES

A. Preparation of the Compounds of the Invention.

Overview

The amide compounds of the invention can conveniently be prepared by acylation of 2-aminobenzo-1,3-thiazoles. The acylation could be performed by treating the 2-aminobenzo-1,3-thiazoles with acetyl chloride or acetyl anhydride (R=CH$_3$) or by treatment of a carboxylic acid (R≠CH$_3$) under coupling conditions (e.g. using HBTU or other coupling reagents typically used for peptide synthesis).

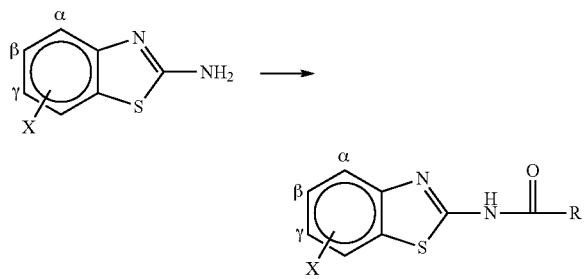

The 2-aminobenzo-1,3-thiazoles themselves can be prepared in a two-step sequence from the corresponding aniline as outlined below. The aniline derivative is treated with potassium thiocyanate forming a thiourea derivative that is subsequently cyclised by addition of bromine.

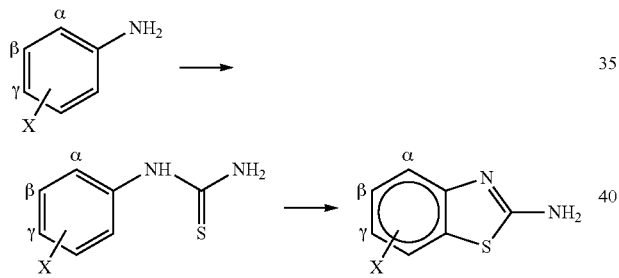

Compounds with a "reversed" amide bond, included as comparative examples, can be prepared from 2-benzo-1,3-thiazole carboxylic acid derivatives by performing a HBTU mediated coupling to a suitable amine or aniline derivative.

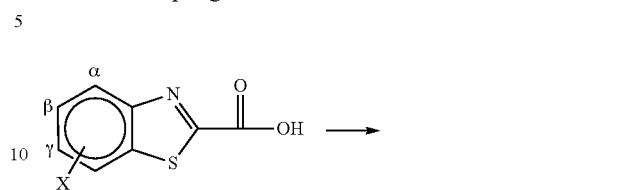

Urea derivatives can be prepared by the reaction between 2-aminobenzo-1,3-thiazole derivatives and suitable alkyl- or aryl isocyanates as shown in the scheme below.

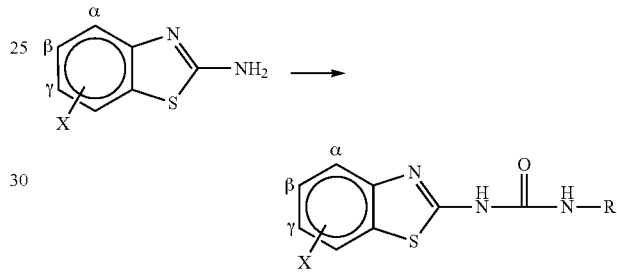

Example 1

N-(5-hydroxybenzo[d]thiazol-2-yl)acetamide

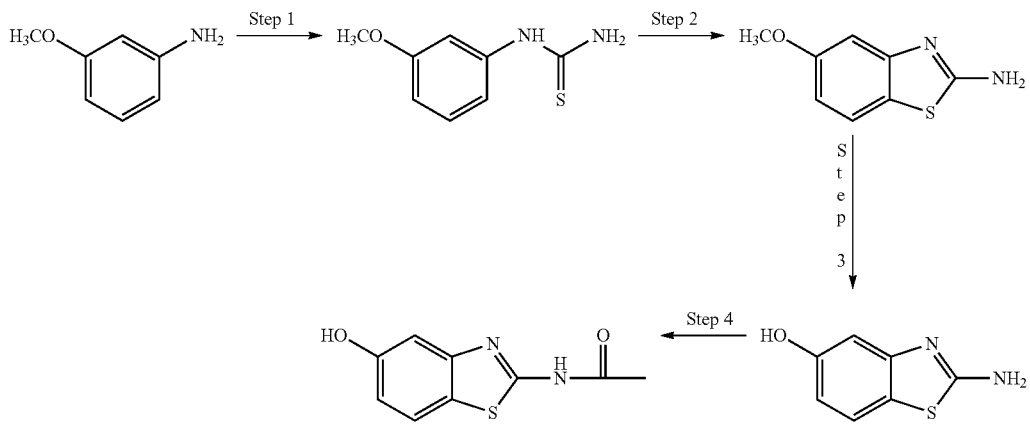

Step 1. 1-(3-methoxyphenyl)thiourea

3-Methoxyaniline (approx 57 mmol) was added to a mixture of sodium thiocyanate (15 eqv) in isopropylacetate (56 mL) at room temperature. Trifluoroacetic acid (11 mL (2.5 eqv)) was then added portionwise ensuring that the temperature of the mixture was maintained at 40° C. or less. The temperature of the mixture was then raised to 85° C. and stirred for 16 hours. The mixture was cooled and 7 mL of distilled water were added before further cooling to 0° C. The crude product was isolated by vacuum filtration. The crude yield was in the range of 80%

Step 2. 5-Methoxybenzo(dithiazol-2-amine

The thiourea above (5.5 mmol) was dissolved in acetic acid (10 mL) and lithium bromide (1.5 eqv) was added at room temperature. Bromine (1 eqv) was added portionwise (the reaction is very exothermic) ensuring that the temperature mixture did not exceed 30° C. The reaction vessel was then heated to 40° C. The reaction is stirred and subsequently cooled room temperature. The product is isolated by vacuum filtration and washed twice with 5% sodium carbonate solution and twice with distilled water before drying. The crude yield was in the range of 75%.

Step 3. 5-Hydroxyoxybenzo[d]thiazol-2-amine

Borontribromide (2 ml) was added to a suspension of 5-methoxybenzo[d]thiazol-2-amine (0.18 mmol) in dichlorormethane at 0° C. before overnight stirring at ambient temperature. The reaction mixture was carefully quenched with water before extraction with ethyl acetate. The crude product was isolated by evaporation of the solvent under reduced pressure.

Step 4. N-(5-Hydroxybenzo[d]thiazol-2-yl)acetamide

The 2-aminobenzothiazole above (0.5 mmol) and acetic anhydride (2.2 eqv.) were dissolved in 2 mL of DMF. DIPEA (3 eqv) was added and the mixture was placed in a microwave oven and irradiated at 60° C. for 2 h. The mixture was triturated into 50 mL of 5% $NaHSO_4$ and stirred for 15 min. The crude product was hydrolysed in 5% NaOH before pH adjustment to 7-7.5 where the N-acetylated product precipitated.

In a similar manner the following products were prepared:

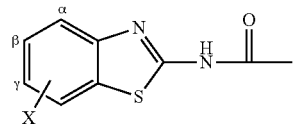

| X | Compound | Calcd mass <MH+> | Obsd mass <MH+> | 1H NMR (Exchangeable protons not reported) |
|---|---|---|---|---|
| γ-OH | 01-71 | 209.03 | 208.9 | $^1$H NMR (400 MHz, Methanol-d4) δ 7.54 (d, J = 8.7 Hz, 1H), 7.20 (d, J = 2.4 Hz, 1H), 6.90 (dd, J = 8.8, 2.5 Hz, 1H), 2.23 (s, 3H). |
| β-OH | 01-66 | 209.03 | 208.9 | $^1$H NMR (400 MHz, Methanol-d4) δ 7.62 (d, J = 8.6 Hz, 1H), 7.14 (d, J = 2.3 Hz, 1H), 6.83 (dd, J = 8.6, 2.3 Hz, 1H), 2.25 (s, 3H). |
| γ-$CF_3$ | 01-90 | 261.03 | 260.8 | $^1$H NMR (400 MHz, DMSO-d6) δ 8.45 (d, J = 1.7 Hz, 1H), 7.88 (d, J = 8.5 Hz, 1H), 7.71 (dd, J = 8.5, 1.9 Hz, 1H), 2.21 (s, 3H). |
| β-$CF_3$ | 03-73 | 261.03 | 260.8 | $^1$H NMR (400 MHz, Methanol-d4) δ 8.04 (d, J = 8.3 Hz, 1H), 8.01-7.95 (m, 1H), 7.59-7.49 (m, 1H), 2.27 (s, 3H). |
| γ-CN | 01-94 | 218.03 | 217.9 | $^1$H NMR (400 MHz, DMSO-d6) δ 8.53 (d, J = 1.6 Hz, 1H), 7.91-7.64 (m, 2H), 2.22 (s, 3H). |
| β-$CH_3$ | 03-76* | 207.05 | 207.2 | $^1$H NMR (400 MHz, DMSO-d6) δ 7.80 (s, 1H), 7.53 (s, 1H), 7.16-7.07 (m, 1H), 2.39 (s, 3H), 2.17 (s, 3H). |
| β-F | 03-77 | 211.03 | 211.3 | $^1$H NMR (400 MHz, DMSO-d6) δ 7.96 (dd, J = 8.7, 5.5 Hz, 1H), 7.53 (dd, J = 10.1, 2.4 Hz, 1H), 7.16 (td, J = 9.0, 2.5 Hz, 1H), 2.19 (s, 3H). |
| H | 03-32* | 193.04 | 193.0 | $^1$H NMR (400 MHz, DMSO-d6) δ 7.94 (s, 1H), 7.71 (s, 1H), 7.41 (s, 1H), 7.28 (s, 1H), 2.18 (s, 3H). |
| β-$OCH_3$ | 03-21 | 223.05 | 223.0 | $^1$H NMR (400 MHz, DMSO-d6) δ 7.79 (d, J = 8.7 Hz, 1H), 7.25 (d, J = 2.4 Hz, 1H), 6.91 (dd, J = 8.8, 2.4 Hz, 1H), 3.80 (s, 4H), 2.17 (s, 3H). |
| γ-F | 03-94 | 211.03 | 210.4 | $^1$H NMR (600 MHz, DMSO-d6) δ 12.36 (s, 1H), 7.87 (dd, J = 8.8, 2.8 Hz, 1H), 7.73 (dd, J = 8.9, 4.8 Hz, 1H), 7.27 (td, J = 9.1, 2.8 Hz, 1H), 2.20 (s, 3H). |
| γ-$NO_2$ | 13-10 | 238.02 | 237.6 | $^1$H NMR (400 MHz, DMSO-d6) δ 9.04 (d, J = 2.5 Hz, 1H), 8.27 (dd, J = 9.0, 2.4 Hz, 1H), 7.88 (d, J = 8.9 Hz, 1H), 2.25 (s, 3H). |
| γ-$OCH_3$ | 03-20 | 223.05 | 223.0 | $^1$H NMR (600 MHz, DMOS-$d_6$) δ 12.19 (s, 1H), 7.62 (d, J = 8.8 Hz, 1H), 7.54 (d, J = 2.6 Hz, 1H), 7.01 (dd, J = 8.8, 2.6 Hz, 1H), 3.80 (s, 3H), 2.18 (s, 3H). |

-continued

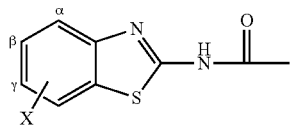

| X | Compound | Calcd mass <MH+> | Obsd mass <MH+> | 1H NMR (Exchangeable protons not reported) |
|---|---|---|---|---|
| γ-CONH$_2$ | 08-70 | 236.05 | 235.6 | $^1$H NMR (600 MHz, DMSO-d$_6$) δ 8.44 (d, J = 1.8 Hz, 1H), 7.92 (dd, J = 8.5, 1.8 Hz, 1H), 7.74 (d, J = 8.4 Hz, 1H), 2.20 (s, 3H). |

\* = comparative example

Example 2

Methyl 3-((6-(trifluoromethyl)benzo[d]thiazol-2-yl)carbamoyl)benzoate

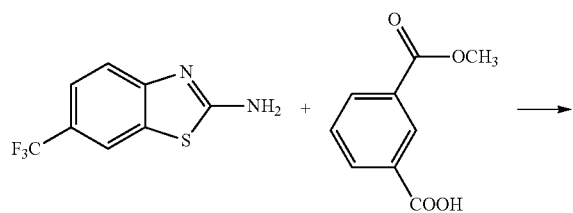

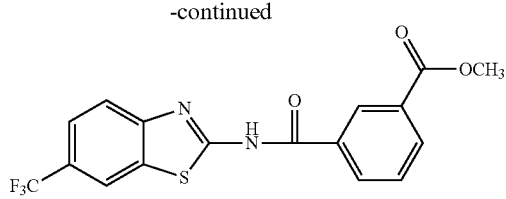

6-(trifluoromethyl)benzo[d]thiazol-2-amine (commercially available or prepared according to Step 1 and 2 of Example 1) (1 eq), 3-(methoxycarbonyl)benzoic acid (1.05 eq) and DIPEA (5 eq) were dissolved in DMF (2 ml). HBTU (1.2 eq) was added and the reaction were stirred overnight at ambient temperature before extraction with ethylacetate, washed thoroughly 2 times with dilute acid and dried. The crude product, methyl 3-((6-(trifluoromethyl)benzo[d]thiazol-2-yl)carbamoyl)benzoate, was isolated by evaporation of the solvent under reduced pressure.

In a similar manner the following products were prepared:

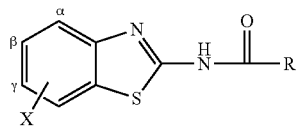

| X | R | Compound | Calcd mass <MH+> | Obsd mass <MH+> | 1H NMR (Exchangeable protons not reported) |
|---|---|---|---|---|---|
| γ-OH | 4-pyridyl | 08-42 | 272.04 | 272.0 | $^1$H NMR (400 MHz, DMSO-d6) δ 8.84 (d, J = 5.4 Hz, 2H), 8.05 (d, J = 5.5 Hz, 2H), 7.58 (d, J = 8.7 Hz, 1H), 7.32 (d, J = 2.4 Hz, 1H), 6.92 (dd, J = 8.7, 2.4 Hz, 1H). |
| γ-OH | 3-pyridyl | 08-44 | 272.04 | 272.1 | $^1$H NMR (400 MHz, DMSO-d6) δ 9.24 (d, J = 2.2 Hz, 1H), 8.82 (dd, J = 5.0, 1.6 Hz, 1H), 8.52 (d, J = 8.1 Hz, 1H), 7.66 (dd, J = 8.0, 4.9 Hz, 1H), 7.57 (d, J = 8.7 Hz, 1H), 7.31 (d, J = 2.4 Hz, 1H), 6.91 (dd, J = 8.7, 2.4 Hz, 1H). |
| γ-OH | 2-pyridyl | 03-12 | 272.04 | 272.1 | $^1$H NMR (400 MHz, Methanol-d4) δ 8.78 (d, J = 4.7 Hz, 1H), 8.33 (d, J = 7.9 Hz, 1H), 8.13 (d, J = 8.3 Hz, 1H), 7.74 (d, J = 7.0 Hz, 1H), 7.61 (d, J = 8.8 Hz, 1H), 7.27 (d, J = 2.3 Hz, 1H), 6.96 (dd, J = 8.8, 2.5 Hz, 1H). |

-continued

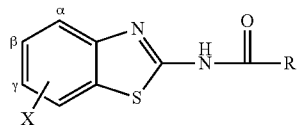

| X | R | Compound | Calcd mass <MH+> | Obsd mass <MH+> | 1H NMR (Exchangeable protons not reported) |
|---|---|---|---|---|---|
| β-OH | 4-pyridyl | 03-11 | 272.04 | 271.7 | ¹H NMR (400 MHz, DMSO-d6) δ 8.86 (d, J = 5.5 Hz, 2H), 8.10 (d, J = 5.2 Hz, 2H), 7.75 (d, J = 8.6 Hz, 1H), 7.10 (d, J = 2.3 Hz, 1H), 6.84 (dd, J = 8.6, 2.2 Hz, 1H). |
| β-OH | 3-pyridyl | 03-33 | 272.04 | 272.1 | ¹H NMR (400 MHz, DMSO-d6) δ 9.23 (d, J = 2.3 Hz, 1H), 8.76 (d, J = 4.8 Hz, 1H), 8.52-8.28 (m, 1H), 7.70 (d, J = 8.5 Hz, 1H), 7.56 (dd, J = 8.0, 4.8 Hz, 1H), 7.08 (d, J = 2.4 Hz, 1H), 6.79 (dd, J = 8.4, 2.4 Hz, 1H). |
| β-OH | 2-pyridyl | 03-13 | 272.04 | 272.1 | ¹H NMR (400 MHz, Methanol-d4) δ 8.82 (d, J = 5.2 Hz, 1H), 8.50 (d, J = 8.0 Hz, 1H), 8.36 (d, J = 8.0 Hz, 1H), 7.90 (t, J = 6.6 Hz, 1H), 7.69 (d, J = 8.7 Hz, 1H), 7.14 (d, J = 2.3 Hz, 1H), 6.92 (dd, J = 8.7, 2.3 Hz, 1H). |
| γ-CF₃ | phenyl | 03-99 | 323.04 | 322.7 | ¹H NMR (400 MHz, Methanol-d4) δ 8.55 (s, 1H), 8.16 (d, J = 7.7 Hz, 2H), 7.95 (d, J = 8.4 Hz, 1H), 7.78 (d, J = 8.5 Hz, 1H), 7.69 (t, J = 7.3 Hz, 1H), 7.58 (t, J = 7.7 Hz, 2H). |
| β-OCH₃ | phenyl | 03-95 | 285.06 | 284.7 | ¹H NMR (400 MHz, Methanol-d4) δ 8.09-7.98 (m, 2H), 7.73 (d, J = 8.7 Hz, 1H), 7.65 (t, J = 7.3 Hz, 1H), 7.56 (t, J = 7.6 Hz, 2H), 7.30 (d, J = 2.5 Hz, 1H), 6.96 (dd, J = 8.6, 2.4 Hz, 1H), 3.86 (s, 3H). |
| γ-OCH₃ | phenyl | 03-98 | 285.06 | 284.5 | ¹H NMR (400 MHz, DMSO-d6) δ 8.08 (d, J = 7.8 Hz, 2H), 7.68-7.60 (m, 2H), 7.59-7.49 (m, 3H), 7.04 (dd, J = 8.8, 2.5 Hz, 1H), 3.80 (s, 3H). |
| β-OH | phenyl | 03-102 | 271.05 | 270.8 | 1H NMR (400 MHz, DMSO-d6) δ 8.12 (d, J = 7.7 Hz, 2H), 7.74 (d, J = 8.6 Hz, 1H), 7.64 (t, J = 7.3 Hz, 1H), 7.55 (t, J = 7.6 Hz, 2H), 7.12 (s, 1H), 6.82 (dd, J = 8.6, 2.3 Hz, 1H). |
| γ-OH | phenyl | 03-60 | 271.05 | 271.0 | ¹H NMR (400 MHz, Methanol-d4) δ 8.05-7.99 (m, 2H), 7.69-7.51 (m, 4H), 7.25 (d, J = 2.4 Hz, 1H), 6.94 (dd, J = 8.8, 2.5 Hz, 1H) |
| γ-CN | phenyl | 03-106 | 280.05 | 279.6 | ¹H NMR (400 MHz, DMSO-d6) δ 8.46 (s, 1H), 8.14 (d, J = 7.4 Hz, 2H), 7.77 (s, 2H), 7.65-7.45 (m, 3H). |

-continued

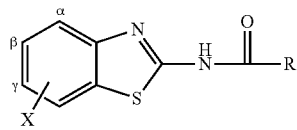

| X | R | Compound | Calcd mass <MH+> | Obsd mass <MH+> | 1H NMR (Exchangeable protons not reported) |
|---|---|---|---|---|---|
| γ-F | phenyl | 03-92 | 273.04 | 272.6 | ¹H NMR (400 MHz, DMSO-d6) δ 8.11 (d, J = 7.6 Hz, 2H), 7.97-7.88 (m, 1H), 7.78 (dd, J = 9.1, 4.8 Hz, 1H), 7.65 (t, J = 7.4 Hz, 1H), 7.55 (t, J = 7.6 Hz, 2H), 7.30 (t, J = 9.3 Hz, 1H). |
| γ-CF₃ | methyl 3-substituted benzoate | 03-105 | 381.05 | 380.7 | ¹H NMR (400 MHz, DMSO-d6) δ 8.72 (s, 1H), 8.53 (s, 1H), 8.39 (d, J = 7.9 Hz, 1H), 8.21 (d, J = 7.8 Hz, 1H), 7.94 (d, J = 8.5 Hz, 1H), 7.81-7.68 (m, 2H), 3.91 (s, 3H). |
| β-OCH₃ | methyl 3-substituted benzoate | 03-108 | 343.07 | 342.8 | ¹H NMR (400 MHz, DMSO-d6) δ 8.72 (s, 1H), 8.37 (d, J = 7.7 Hz, 1H), 8.14 (d, J = 7.5 Hz, 1H), 7.78 (d, J = 8.6 Hz, 1H), 7.66 (t, J = 7.7 Hz, 1H), 7.21 (s, 1H), 6.89 (d, J = 8.6 Hz, 1H), 3.89 (s, 3H), 3.81 (s, 3H). |
| γ-F | methyl 3-substituted benzoate | 03-110 | 331.05 | 330.7 | ¹H NMR (400 MHz, DMSO-d6) δ 8.73 (s, 1H), 8.39 (d, J = 7.8 Hz, 1H), 8.16 (d, J = 7.7 Hz, 1H), 7.85 (dd, J = 8.7, 2.7 Hz, 1H), 7.70 (dq, J = 11.5, 7.7, 6.2 Hz, 2H), 7.26 (td, J = 9.1, 2.7 Hz, 1H), 3.91 (s, 3H). |
| β-OCH₃ | 3-substituted benzamide | 03-113 | 328.07 | 327.8 | 1H NMR (400 MHz, DMSO-d6) δ 8.63 (s, 1H), 8.23 (d, J = 7.8 Hz, 1H), 8.11 (s, 1H), 8.07 (d, J = 7.9 Hz, 1H), 7.80 (s, 1H), 7.60 (t, J = 7.8 Hz, 1H), 7.50 (s, 1H), 7.24 (s, 1H), 6.92 (s, 1H), 3.82 (s, 3H). |
| β-OCH₃ | 4-acetamidophenyl | MS: LY-2-77 | 342.09 | 341.8 | ¹H-NMR (300 MHz; DMSO-d₆): δ 8.11 (d, J = 8.7 Hz, 2H), 7.86 (dd, J = 8.7, 0.1 Hz, 1H), 7.75 (d, J = 8.7 Hz, 2H), 7.29-7.28 (m, 1H), 6.97 (dd, J = 8.7, 2.4 Hz, 1H), 3.84 (s, 3H), 2.10 (s, 3H) |
| γ-OH | 2-acetamidophenyl | 08-39 | 328.07 | 328.1 | |
| β-OH | 3-acetamidophenyl | MS: LY-2-89 | 328.07 | 327.8 | ¹H-NMR (400 MHz; DMSO-d₆): δ 8.30 (s, 1H), 7.84-7.82 (m, 2H), 7.75 (d, J = 8.6 Hz, 1H), 7.47 (t, J = 7.9 Hz, 1H), 7.13 (s, 1H), 6.83 (d, J = 8.6 Hz, 1H), 2.09 (s, 3H) |

-continued

| X | R | Compound | Calcd mass <MH+> | Obsd mass <MH+> | 1H NMR (Exchangeable protons not reported) |
|---|---|---|---|---|---|
| γ-OH | *(3-acetamidophenyl)* | 03-58 | 328.07 | 327.9 | ¹H NMR (400 MHz, DMSO-d6) δ 8.24 (s, 1H), 7.79 (d, J = 7.2 Hz, 2H), 7.56 (d, J = 8.7 Hz, 1H), 7.44 (t, J = 8.0 Hz, 1H), 7.30 (d, J = 2.5 Hz, 1H), 6.90 (dd, J = 8.6, 2.5 Hz, 1H), 2.06 (s, 3H). |
| β-OCH₃ | *(3-acetamidophenyl)* | MS. LY-2-85 | 342.09 | 341.9 | ¹H-NMR (300 MHz; DMSO-d₆): δ 8.30 (s, 1H), 7.85 (m, 3H), 7.47 (t, J = 7.8 Hz, 1H), 7.29 (d, J = 2.3 Hz, 1H), 6.98 (dd, J = 8.7, 2.3 Hz, 1H), 3.84 (s, 3H), 2.09 (s, 3H). |
| β-OH | *(4-acetamidophenyl)* | MS: LY-2-87 | 328.07 | 327.8 | ¹H-NMR (400 MHz; DMSO-d₆): δ 8.10 (d, J = 8.7 Hz, 2H), 7.74 (d, J = 8.6 Hz, 3H), 7.12 (d, J = 2.2 Hz, 1H), 6.82 (dd, J = 8.7, 2.2 Hz, 1H), 2.10 (s, 3H) |
| γ-OH | *(4-acetamidophenyl)* | 03-74 | 328.07 | 328.3 | ¹H NMR (400 MHz, Methanol-d4) δ 8.00 (d, J = 8.4 Hz, 2H), 7.72 (d, J = 8.3 Hz, 2H), 7.54 (d, J = 8.7 Hz, 1H), 7.22 (s, 1H), 6.9 (d, J = 8.4 Hz, 1H), 2.13 (s, 3H). |
| γ-CF₃ | *(1-acetamidoethyl)* | 03-80 | 332.06 | 331.9 | ¹H NMR (400 MHz, Methanol-d4) δ 8.24 (s, 1H), 7.87 (d, J = 8.6 Hz, 1H), 7.69 (d, J = 8.6 Hz, 1H), 4.59 (q, J = 7.2, 6.5 Hz, 1H), 2.02 (s, 3H), 1.46 (d, J = 7.2, Hz, 3H). |

Example 3. (Comparative Example)

N-(3-acetamidophenyl)-6-hydroxybenzo[d]thiazole-2-carboxamide

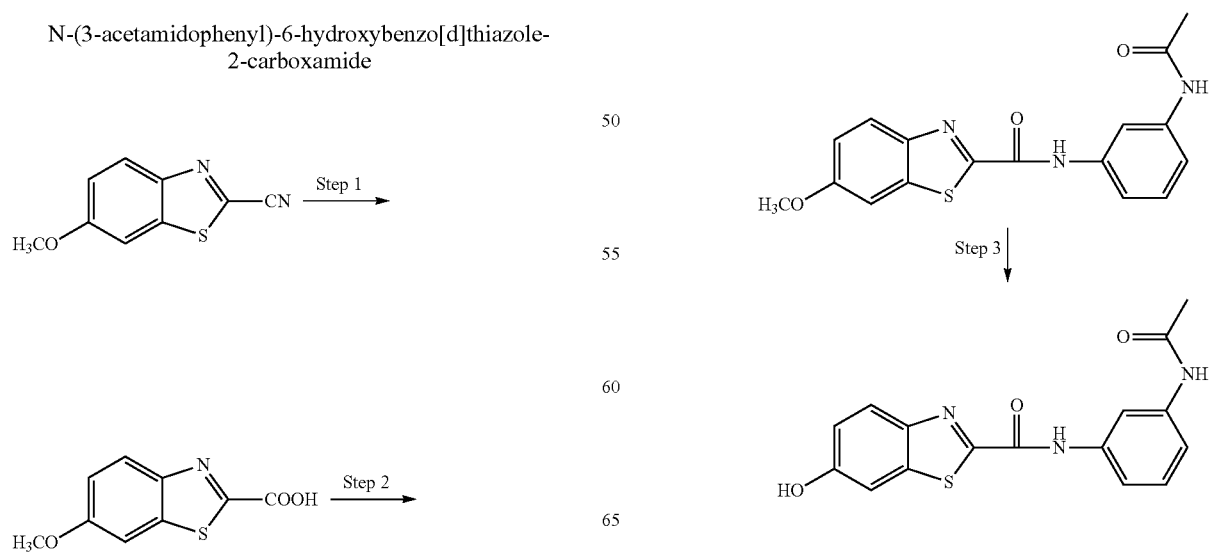

Step 1. 6-Methoxybenzo[d]thiazol-2-carboxylic acid

6-Methoxybenzo[d]thiazole-2-carbonitrile (1 mmol) and concentrated HCl (5 ml) was placed in a sealed microwave vial and heated at 90° C. for one hour with the microwave set for a high-absorbance mixture. The mixture was then diluted with water and the product was isolated by vacuum evaporation.

Step 2. N-(3-acetamidophenyl)-6-methoxybenzo[d]thiazole-2-carboxamide

3-Acetamidoaniline (1 eq), 6-methoxybenzo[d]thiazol-2-carboxylic acid (1.05 mmol) and DIPEA (5 mmol) were dissolved in DMF (2 ml). HBTU (1.2 mmol) was added and the reaction were stirred overnight at ambient temperature before extraction with ethyl acetate and washed thoroughly dilute acid and dried. The crude product was isolated by evaporation under vacuum.

Step 3. N-(3-acetamidophenyl)-6-hydroxybenzo[d]thiazole-2-carboxamide

Borontribromide (2 ml) was added to a suspension of N-(3-acetamidophenyl)-6-methoxybenzo[d]thiazole-2-carboxamide (0.18 mmol) in dichlorormethane at 0° C. before overnight stirring at ambient temperature. The reaction mixture was carefully quenched with water before extraction with ethyl acetate. The crude product was isolated by evaporation under vacuum.

In a similar manner the following products were prepared:

Example 4

1-(6-fluorobenzo[d]thiazol-2-yl)-3-phenylurea

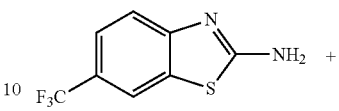

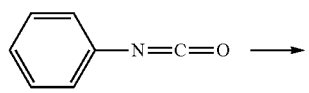

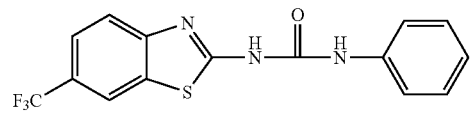

Phenyl isocyanate (107 mg, 0.9 mmol) was added to a solution of 2-amino-6-fluorobenzothiazole (100 mg, 0.6 mmol) in dry DCM under argon. The reaction was allowed to proceed at R.T. for 16 hours before the product was isolated by filtration.

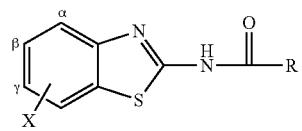

| X | R | Compound | Calcd mass <MH+> | Obsd mass <MH+> | 1H NMR (Exchangeable protons not reported) |
|---|---|---|---|---|---|
| γ-OH | 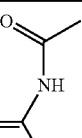 | 03-07 | 328.37 | 328.0 | $^1$H NMR (400 MHz, DMSO-d6) δ 8.16 (d, J = 2.1 Hz, 1H), 7.99 (d, J = 8.9 Hz, 1H), 7.48 (d, J = 2.4 Hz, 1H), 7.44 (d, J = 8.1 Hz, 1H), 7.39 (d, J = 8.1 Hz, 1H), 7.25 (t, J = 8.1 Hz, 1H), 7.10 (dd, J = 9.0, 2.4 Hz, 1H), 2.03 (s, 3H). |
| γ-OCH$_3$ | 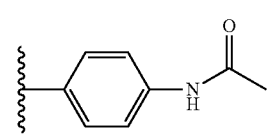 [SMILES: *c1ccc(NC(C)=O)cc1] | 03-17 | 342.09 | 342.1 | $^1$H NMR (400 MHz, DMSO-d6) δ 8.07 (d, J = 9.1 Hz, 1H), 7.80 (d, J = 8.6 Hz, 3H), 7.56 (d, J = 8.5 Hz, 2H), 7.24 (dd, J = 8.8, 2.7 Hz, 1H), 3.88 (s, 3H), 2.03 (s, 3H). |
| γ-OCH$_3$ | 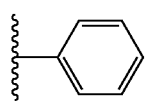 | 13-03 | 285.06 | 285.0 | $^1$H NMR (400 MHz, DMSO-d6) δ 8.08 (d, J = 9.0 Hz, 1H), 7.88 (d, J = 8.1 Hz, 2H), 7.81 (d, J = 2.6 Hz, 1H), 7.37 (d, J = 7.8 Hz, 2H), 7.24 (dd, J = 9.1, 2.6 Hz, 1H), 7.14 (t, J = 7.4 Hz, 1H), 3.87 (s, 3H). |

In a similar manner the following product was prepared:

| X | R | Compound | Calcd mass <MH+> | Obsd mass <MH+> | 1H NMR (Exchangeable protons not reported) |
|---|---|---|---|---|---|
| β-OH | ⸺NH⸺(3-OCH₃-phenyl) | 13-62 | 316.07 | 315.9 | ¹H NMR (400 MHz, DMSO-d6) δ 7.61 (d, J = 8.5 Hz, 1H), 7.21 (d, J = 9.2 Hz, 2H), 7.01 (d, J = 8.0 Hz, 2H), 6.71 (d, J = 8.3 Hz, 1H), 6.61 (d, J = 8.1 Hz, 1H), 3.76 (s, 3H). |

B. Kinase Activity
1. Profiling Kinase Inhibitory Activity
DYRK 1A Assay.

DYRK 1A (5-20 mU of diluted in 50 mM Tris pH7.5, 0.1 mM EGTA) is assayed against Woodtide (KKISGRL-SPIMTEQ) (SEQ ID NO. 1) in a final volume of 25.5 μl containing 50 mM Tris pH 7.5, 0.1 mM EGTA, 350 μM substrate peptide, 10 mM Magnesium acetate and 0.05 mM [33P-g-ATP](50-1000 cpm/pmole) and incubated for 30 min at room temperature. Assays are stopped by addition of 5 μl of 0.5 M (3%) orthophosphoric acid and then harvested onto P81 Unifilter plates with a wash buffer of 50 mM orthophosphoric acid.

Similar assays were performed for the other kinases in the tables which follow using the ADP-Glo™ kinase assay of Promega (products V9101, V9102, V9103 and V9 104).

Results

Data showing residual kinase activity at 100 micromolar inhibitor concentration is given in the tables which follows. The values are on an absolute scale such that 100 is no change in the presence of putatitic inhibitor, any value over 100 shows kinase activation. Any value less that 25 is considered to be highly significant inhibition.

Results for Compounds of Example 1 (Except 03-20 and 08-70)

| Kinase | 01-71 | 01-66 | 01-90 | 03-73 | 01-94 | 03-76 | 03-77 | 03-32 | 03-21 | 03-94 | 13-10 |
|---|---|---|---|---|---|---|---|---|---|---|---|
| MKK1 | 35 | 31 | 80 | 96 | 34 | 73 | 87 | 81 | 64 | 76 | 62 |
| MKK2 | 48 | 42 | 73 | 98 | 54 | 155 | 101 | 96 | 90 | | |
| MKK6 | 78 | 70 | 85 | 120 | 98 | 113 | 118 | 85 | 117 | | |
| ERK1 | 65 | 61 | 100 | 83 | 97 | 91 | 90 | 83 | 87 | | |
| ERK2 | 83 | 104 | 102 | 108 | 91 | 96 | 99 | 149 | 109 | | |
| ERK5 | | | | 67 | | 62 | 38 | 66 | 57 | | |
| JNK1 | 72 | 53 | 104 | 120 | 90 | 97 | 80 | 97 | 97 | 82 | 82 |
| JNK2 | 82 | 63 | 87 | 111 | 82 | 105 | 99 | 105 | 92 | | |
| JNK3 | 66 | 37 | 76 | 83 | 53 | 76 | 68 | 66 | 80 | | |
| p38a MAPK | 86 | 84 | 106 | 92 | 102 | 92 | 88 | 91 | 96 | 84 | 103 |
| p38b MAPK | 106 | 92 | 82 | 97 | 100 | 83 | 79 | 107 | 101 | | |
| p38g MAPK | 84 | 46 | 101 | 93 | 82 | 92 | 77 | 109 | 56 | | |
| p38d MAPK | 43 | 70 | 76 | 52 | 69 | 85 | 76 | 80 | 75 | | |
| RSK1 | 25 | 44 | 74 | 89 | 51 | 78 | 72 | 86 | 93 | 85 | 89 |
| RSK2 | 48 | 66 | 92 | 83 | 87 | 96 | 83 | 105 | 94 | | |
| PDK1 | 63 | 69 | 93 | 105 | 97 | 93 | 91 | 96 | 115 | 87 | 93 |
| PKBa | 87 | 87 | 104 | 106 | 95 | 104 | 95 | 104 | 91 | 94 | 101 |
| PKBb | 57 | 55 | 100 | 104 | 98 | 91 | 93 | 112 | 92 | | |
| SGK1 | 33 | 77 | 69 | 77 | 40 | 65 | 66 | 92 | 82 | 67 | 58 |
| S6K1 | 23 | 54 | 85 | 77 | 73 | 77 | 48 | 92 | 63 | 67 | 65 |
| PKA | 70 | 95 | 87 | 124 | 93 | 105 | 95 | 91 | 11 | 93 | 99 |
| ROCK 2 | 34 | 56 | 80 | 83 | 69 | 79 | 37 | 91 | 52 | 70 | 96 |
| PRK2 | 36 | 67 | 94 | 91 | 70 | 84 | 74 | 81 | 67 | 80 | 93 |
| PKCa | 77 | 82 | 101 | 111 | 93 | 94 | 101 | 104 | 101 | 98 | 93 |
| PKCγ | 76 | 99 | 53 | 106 | 83 | 106 | 102 | 94 | 103 | | |
| PKCz | 74 | 98 | 81 | 97 | 80 | 101 | 110 | 126 | 85 | | |
| PKD1 | 37 | 30 | 119 | 83 | 97 | 89 | 66 | 105 | 59 | 105 | 82 |
| STK33 | 41 | 52 | 46 | 86 | 35 | 80 | 70 | 104 | 81 | | |
| MSK1 | 31 | 62 | 87 | 91 | 81 | 84 | 74 | 98 | 93 | 88 | 92 |
| MNK1 | 28 | 17 | 65 | 89 | 47 | 81 | 64 | 89 | 77 | | |
| MNK2 | 34 | 33 | 71 | 96 | 50 | 81 | 86 | 91 | 84 | | |
| MAPKAP-K2 | 46 | 77 | 90 | 114 | 65 | 105 | 106 | 102 | 108 | | |
| MAPKAP-K3 | 34 | 39 | 101 | 93 | 101 | 106 | 107 | 61 | 97 | | |

-continued

| Kinase | 01-71 | 01-66 | 01-90 | 03-73 | 01-94 | 03-76 | 03-77 | 03-32 | 03-21 | 03-94 | 13-10 |
|---|---|---|---|---|---|---|---|---|---|---|---|
| PRAK | 47 | 58 | 111 | 87 | 69 | 75 | 76 | 78 | 71 | | |
| CAMKKb | 57 | 44 | 29 | 65 | 35 | 71 | 74 | 101 | 87 | 67 | 73 |
| CAMK1 | 52 | 69 | 64 | 89 | 80 | 90 | 106 | 99 | 81 | 86 | 84 |
| SmMLCK | 39 | 58 | 80 | 71 | 54 | 62 | 66 | 81 | 50 | 67 | 58 |
| PHK | 47 | 49 | 52 | 91 | 63 | 87 | 89 | 94 | 111 | | |
| DAPK1 | 21 | 44 | 85 | 93 | 41 | 82 | 82 | 89 | 79 | | |
| CHK1 | 82 | 75 | 97 | 110 | 96 | 102 | 103 | 105 | 110 | | |
| CHK2 | 17 | 31 | 43 | 78 | 30 | 65 | 63 | 87 | 58 | 74 | 59 |
| CDK2-Cyclin A | 30 | 71 | 22 | 96 | 11 | 72 | 66 | 76 | 93 | | |
| CDK9-Cyclin T1 | 48 | 85 | 26 | 97 | 15 | 49 | 46 | 45 | 90 | | |
| PLK1 | 97 | 103 | 80 | 91 | 108 | 90 | 78 | 62 | 90 | 93 | 96 |
| Aurora A | 68 | 87 | 81 | 96 | 61 | 109 | 100 | 109 | 103 | | |
| TLK1 | 45 | 92 | 82 | 103 | 53 | 106 | 89 | 92 | 97 | | |
| LKB1 | 17 | 38 | 79 | 98 | 35 | 96 | 85 | 97 | 93 | 46 | 73 |
| AMPK | 37 | 61 | 90 | 75 | 73 | 77 | 73 | 107 | 100 | | |
| AMPK (hum) | | | 74 | 62 | 40 | 69 | 80 | 86 | 81 | 59 | 70 |
| MARK1 | 33 | 56 | 90 | 88 | 60 | 94 | 80 | 77 | 98 | | |
| MARK2 | 54 | 63 | 74 | 99 | 53 | 97 | 79 | 88 | 103 | | |
| MARK3 | 46 | 34 | 61 | 63 | 50 | 71 | 58 | 85 | 72 | 96 | 85 |
| MARK4 | 66 | 80 | 66 | 97 | 51 | 80 | 86 | 91 | 100 | | |
| BRSK1 | 16 | 48 | 83 | 83 | 62 | 75 | 78 | 95 | 85 | | |
| BRSK2 | 22 | 56 | 64 | 98 | 67 | 79 | 77 | 91 | 95 | | |
| MELK | 24 | 17 | 49 | 91 | 34 | 58 | 67 | 83 | 44 | | |
| NUAK1 | 26 | 44 | 66 | 74 | 46 | 58 | 66 | 74 | 84 | | |
| SIK2 | 32 | 56 | 72 | 91 | 70 | 71 | 64 | 81 | 89 | | |
| SIK3 | 46 | 57 | 82 | 103 | 73 | 103 | 89 | 89 | 121 | | |
| TSSK1 | 67 | 65 | 90 | 71 | 55 | 79 | 84 | 83 | 75 | | |
| CK1γ2 | 10 | 6 | 59 | 79 | 18 | 54 | 22 | 41 | 6 | | |
| CK2 | 23 | 54 | 92 | 105 | 66 | 75 | 81 | 96 | 87 | 91 | 51 |
| TTBK1 | 61 | 68 | 88 | 94 | 73 | 84 | 80 | 80 | 93 | | |
| TTBK2 | | | 98 | 91 | 78 | 97 | 93 | 85 | 84 | | |
| DYRK1A | 20 | 5 | 8 | 22 | 9 | 23 | 7 | 43 | 2 | 12 | 6 |
| NEK2a | 75 | 85 | 78 | 94 | 60 | 95 | 90 | 90 | 93 | | |
| NEK6 | 75 | 82 | 107 | 119 | 86 | 107 | 96 | 92 | 108 | 92 | 92 |
| IKKb | 63 | 62 | 75 | 94 | 58 | 59 | 61 | 75 | 98 | | |
| IKKe | 58 | 68 | 81 | 93 | 64 | 89 | 91 | 109 | 91 | | |
| TBK1 | 43 | 60 | 83 | 64 | 41 | 78 | 74 | 88 | 81 | 91 | 89 |
| PIM1 | 19 | 12 | 71 | 10 | 26 | 21 | 19 | 79 | 8 | 40 | 81 |
| PIM2 | 38 | 16 | 94 | 63 | 73 | 82 | 62 | 100 | 48 | | |
| SRPK1 | 44 | 59 | 41 | 72 | 47 | 73 | 65 | 59 | 84 | 75 | 62 |
| EF2K | 75 | 76 | 103 | 109 | 98 | 110 | 99 | 89 | 105 | 96 | 95 |
| EIF2AK3 | 77 | 59 | 105 | 100 | 78 | 97 | 99 | 104 | 82 | | |
| HIPK1 | 76 | 97 | 48 | 74 | 37 | 53 | 40 | 62 | 39 | | |
| HIPK2 | 14 | 20 | 16 | 51 | 23 | 51 | 22 | 51 | 25 | 27 | 8 |
| HIPK3 | 27 | 37 | 69 | 106 | 38 | 79 | 62 | 78 | 86 | | |
| PAK2 | 102 | 93 | 103 | 85 | 101 | 102 | 11 | 90 | 95 | | |
| PAK4 | 51 | 66 | 67 | 71 | 34 | 101 | 97 | 75 | 94 | 66 | 86 |
| PAK5 | 85 | 72 | 82 | 85 | 70 | 107 | 111 | 74 | 110 | | |
| PAK6 | 81 | 90 | 106 | 11 | 92 | 108 | 106 | 92 | 108 | | |
| MST2 | 56 | 69 | 99 | 80 | 56 | 75 | 80 | 88 | 91 | 91 | 97 |
| MST3 | 66 | 79 | 85 | 89 | 71 | 85 | 87 | 87 | 91 | | |
| MST4 | 70 | 84 | 89 | 91 | 75 | 103 | 88 | 110 | 88 | | |
| GCK | 19 | 32 | 15 | 36 | 11 | 35 | 8 | 39 | 3 | | |
| MAP4K3 | | | 65 | 63 | 52 | 80 | 55 | 90 | 75 | | |
| MAP4K5 | | | 40 | 73 | 38 | 83 | 65 | 95 | 96 | | |
| MINK1 | 28 | 48 | 35 | 77 | 40 | 63 | 65 | 92 | 61 | | |
| MEKK1 | 96 | 94 | 90 | 111 | 94 | 107 | 102 | 93 | 113 | | |
| MLK1 | 11 | 39 | 39 | 75 | 34 | 57 | 58 | 72 | 84 | | |
| MLK3 | 15 | 41 | 51 | 57 | 55 | 35 | 44 | 71 | 59 | 46 | 54 |
| TESK1 | 61 | 94 | 93 | 115 | 90 | 106 | 106 | 95 | 104 | | |
| TAO1 | 29 | 30 | 71 | 88 | 46 | 76 | 69 | 73 | 72 | | |
| ASK1 | 53 | 70 | 35 | 83 | 18 | 23 | 54 | 66 | 97 | | |
| TAK1 | 11 | 30 | 83 | 45 | 17 | 52 | 46 | 76 | 50 | 26 | 58 |
| IRAK1 | 26 | 29 | 43 | 85 | 11 | 59 | 46 | 65 | 45 | | |
| IRAK4 | 13 | 18 | 12 | 60 | 10 | 51 | 43 | 65 | 52 | 44 | 8 |
| RIPK2 | 22 | 29 | 23 | 48 | 17 | 60 | 64 | 70 | 29 | 38 | 27 |
| OSR1 | 78 | 95 | 75 | 113 | 79 | 116 | 109 | 112 | 119 | | |
| TTK | 31 | 39 | 49 | 86 | 33 | 49 | 64 | 71 | 67 | 37 | 55 |
| MPSK1 | 77 | 80 | 105 | 97 | 94 | 91 | 86 | 86 | 97 | | |
| WNK1 | 96 | 101 | 100 | 128 | 101 | 104 | 99 | 98 | 121 | | |
| ULK1 | | | 87 | 91 | 92 | 82 | 83 | 102 | 103 | | |
| ULK2 | | | 78 | 88 | 68 | 88 | 83 | 92 | 86 | | |
| TGFBR1 | | | | 118 | | 98 | 96 | 92 | 124 | | |

-continued

| Kinase | 01-71 | 01-66 | 01-90 | 03-73 | 01-94 | 03-76 | 03-77 | 03-32 | 03-21 | 03-94 | 13-10 |
|---|---|---|---|---|---|---|---|---|---|---|---|
| Src | 57 | 45 | 63 | 74 | 94 | 79 | 80 | 113 | 86 | 76 | 85 |
| Lck | 192 | 69 | 53 | 101 | 168 | 120 | 96 | 91 | 109 | 92 | 79 |
| CSK | 78 | 92 | 61 | 91 | 83 | 101 | 98 | 83 | 104 | | |
| YES1 | 59 | 72 | 57 | 108 | 86 | 104 | 85 | 93 | 93 | | |
| ABL | 17 | 29 | 31 | 109 | 31 | 82 | 86 | 86 | 111 | | |
| BTK | 69 | 67 | 73 | 93 | 98 | 92 | 105 | 100 | 102 | 107 | 96 |
| JAK2 | 43 | 65 | 73 | 96 | 33 | 51 | 57 | 66 | 88 | 49 | 91 |
| SYK | 71 | 82 | 100 | 74 | 86 | 72 | 82 | 116 | 72 | 96 | 97 |
| ZAP70 | 126 | 113 | 122 | 115 | 118 | 110 | 109 | 111 | 98 | | |
| TIE2 | 65 | 75 | 60 | 92 | 85 | 95 | 112 | 112 | 91 | | |
| BRK | 22 | 77 | 99 | 106 | 100 | 80 | 91 | 89 | 62 | | |
| EPH-A2 | 66 | 67 | 67 | 99 | 73 | 93 | 106 | 111 | 89 | 94 | 65 |
| EPH-A4 | 77 | 73 | 45 | 103 | 62 | 91 | 100 | 111 | 98 | | |
| EPH-B1 | 86 | 93 | 91 | 114 | 94 | 103 | 103 | 97 | 99 | | |
| EPH-B2 | 59 | 70 | 38 | 98 | 42 | 108 | 114 | 116 | 96 | | |
| EPH-B3 | 66 | 83 | 89 | 114 | 72 | 107 | 113 | 71 | 106 | | |
| EPH-B4 | 98 | 83 | 55 | 101 | 62 | 109 | 112 | 99 | 98 | | |
| FGF-R1 | 42 | 67 | 40 | 109 | 51 | 106 | 103 | 12 | 104 | | |
| HER4 | 36 | 40 | 97 | 110 | 90 | 85 | 92 | 78 | 94 | 101 | 81 |
| IGF-1R | 18 | 26 | 84 | 77 | 78 | 75 | 58 | 74 | 78 | 92 | 91 |
| IR | 35 | 63 | 84 | 102 | 81 | 97 | 87 | 87 | 109 | | |
| IRR | 34 | 30 | 49 | 61 | 42 | 66 | 57 | 63 | 47 | | |
| TrkA | 42 | 57 | 45 | 74 | 87 | 56 | 59 | 77 | 78 | 58 | 98 |
| DDR2 | 56 | 65 | 62 | 111 | 93 | 110 | 101 | 97 | 102 | | |
| VEG-FR | 9 | 24 | 8 | 33 | 11 | 50 | 48 | 66 | 71 | 18 | 5 |
| PDGFRA | | | 30 | 34 | 40 | 59 | 59 | 78 | 87 | | |

Results for Compounds of Example 2

| Kinase | 08-42 | 08-44 | 03-12 | 03-11 | 03-33 | 03-13 | 03-99 | 03-95 | 03-98 | 03-102 | 03-60 | 03-106 | 03-92 | 03-105 | 03-108 | 03-110 | 03-113 |
|---|---|---|---|---|---|---|---|---|---|---|---|---|---|---|---|---|---|
| MKK1 | 87 | 67 | 80 | 88 | 89 | 107 | 87 | 92 | 105 | 52 | 49 | 58 | 93 | 86 | 94 | 70 | 119 |
| MKK2 | 72 | 48 | 82 | 98 | 85 | 82 | | | | | 90 | | | | | | |
| MKK6 | 101 | 107 | 99 | 101 | 122 | 105 | | | | | 109 | | | | | | |
| ERK1 | 84 | 81 | 74 | 88 | 93 | 97 | | | | | 67 | | | | | | |
| ERK2 | 73 | 75 | 88 | 85 | 107 | 100 | | | | | 82 | | | | | | |
| ERK5 | 41 | 43 | 53 | 58 | 58 | 51 | | | | | 30 | | | | | | |
| JNK1 | 99 | 102 | 105 | 95 | 111 | 93 | 86 | 90 | 95 | 83 | 88 | 84 | 94 | 84 | 93 | 98 | 86 |
| JNK2 | 90 | 90 | 101 | 93 | 92 | 103 | | | | | 107 | | | | | | |
| JNK3 | 65 | 64 | 70 | 77 | 76 | 67 | | | | | 48 | | | | | | |
| p38a MAPK | 99 | 108 | 107 | 106 | 105 | 96 | 86 | 82 | 86 | 57 | 74 | 60 | 114 | 84 | 94 | 106 | 113 |
| p38b MAPK | 86 | 89 | 105 | 97 | 87 | 91 | | | | | 76 | | | | | | |
| p38g MAPK | 87 | 77 | 89 | 93 | 85 | 94 | | | | | 58 | | | | | | |
| p38d MAPK | 65 | 62 | 77 | 82 | 103 | 99 | | | | | 75 | | | | | | |
| RSK1 | 47 | 41 | 67 | 83 | 73 | 70 | 92 | 64 | 74 | 41 | 28 | 96 | 79 | 87 | 70 | 70 | 87 |
| RSK2 | 62 | 56 | 53 | 71 | 85 | 72 | | | | | 34 | | | | | | |
| PDK1 | 83 | 77 | 88 | 100 | 100 | 104 | 84 | 89 | 101 | 74 | 98 | 106 | 91 | 87 | 101 | 123 | 101 |
| PKBa | 90 | 83 | 74 | 88 | 100 | 107 | 91 | 80 | 103 | 88 | 79 | 67 | 99 | 92 | 106 | 109 | 89 |
| PKBb | 52 | 45 | 61 | 82 | 93 | 60 | | | | | 86 | | | | | | |
| SGK1 | 60 | 51 | 88 | 84 | 86 | 74 | 69 | 60 | 78 | 86 | 41 | 77 | 93 | 86 | 83 | 87 | 88 |
| S6K1 | 38 | 17 | 50 | 83 | 75 | 71 | 86 | 77 | 76 | 42 | 11 | 78 | 79 | 78 | 95 | 91 | 79 |
| PKA | 91 | 92 | 97 | 110 | 102 | 102 | 96 | 83 | 90 | 93 | 97 | 91 | 96 | 96 | 92 | 93 | 101 |
| ROCK 2 | 43 | 42 | 68 | 80 | 53 | 96 | 97 | 54 | 66 | 47 | 11 | 125 | 95 | 103 | 52 | 86 | 68 |
| PRK2 | 44 | 46 | 66 | 77 | 85 | 97 | 85 | 84 | 91 | 68 | 27 | 105 | 95 | 109 | 100 | 85 | 98 |
| PKCa | 81 | 67 | 101 | 91 | 105 | 112 | 114 | 53 | 89 | 72 | 97 | 100 | 96 | 96 | 85 | 109 | 103 |
| PKCγ | 93 | 73 | 143 | 101 | 103 | 141 | | | | | 83 | | | | | | |
| PKCz | 76 | 81 | 88 | 86 | 105 | 102 | | | | | 80 | | | | | | |
| PKD1 | 63 | 54 | 70 | 74 | 71 | 76 | 114 | 92 | 104 | 60 | 47 | 86 | 111 | 90 | 102 | 88 | 110 |
| STK33 | 67 | 57 | 65 | 77 | 70 | 71 | | | | | 38 | | | | | | |
| MSK1 | 92 | 49 | 90 | 97 | 92 | 100 | 70 | 67 | 90 | 72 | 31 | 64 | 81 | 84 | 88 | 77 | 65 |
| MNK1 | 53 | 19 | 67 | 45 | 21 | 100 | | | | | 18 | | | | | | |
| MNK2 | 33 | 36 | 66 | 75 | 36 | 66 | | | | | 25 | | | | | | |

-continued

| Kinase | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| MAPKAP-K2 | 72 | 56 | 43 | 82 | 109 | 98 | | | | | 59 | | | | | | |
| MAPKAP-K3 | 51 | 38 | 31 | 68 | 97 | 62 | | | | | 92 | | | | | | |
| PRAK | 74 | 60 | 65 | 86 | 83 | 90 | | | | | 39 | | | | | | |
| CAMKKb | 68 | 59 | 41 | 88 | 69 | 69 | 86 | 54 | 45 | 32 | 37 | 67 | 80 | 48 | 80 | 62 | 70 |
| CAMK1 | 68 | 42 | 47 | 85 | 104 | 111 | 84 | 76 | 68 | 72 | 22 | 69 | 97 | 92 | 96 | 99 | 102 |
| SmMLCK | 33 | 19 | 9 | 63 | 52 | 37 | 89 | 48 | 75 | 15 | 15 | 94 | 68 | 63 | 79 | 55 | 83 |
| PHK | 58 | 43 | 37 | 63 | 74 | 28 | | | | | 33 | | | | | | |
| DAPK1 | 32 | 26 | 25 | 62 | 82 | 58 | | | | | 19 | | | | | | |
| CHK1 | 70 | 78 | 90 | 78 | 106 | 88 | | | | | 72 | | | | | | |
| CHK2 | 22 | 16 | 23 | 93 | 46 | 75 | 94 | 98 | 37 | 26 | 5 | 62 | 80 | 89 | 65 | 51 | 98 |
| CDK2-Cyclin A | 72 | 72 | 87 | 98 | 92 | 91 | | | | | 78 | | | | | | |
| CDK9-Cyclin T1 | 66 | 43 | 76 | 68 | 97 | 93 | | | | | 76 | | | | | | |
| PLK1 | 74 | 63 | 65 | 76 | 80 | 96 | 112 | 77 | 102 | 83 | 74 | 103 | 92 | 101 | 96 | 108 | 105 |
| Aurora A | 103 | 99 | 95 | 106 | 108 | 93 | | | | | 82 | | | | | | |
| TLK1 | 97 | 90 | 96 | 95 | 97 | 99 | | | | | 74 | | | | | | |
| LKB1 | 65 | 45 | 64 | 87 | 83 | 45 | 103 | 72 | 118 | 33 | 68 | 107 | 100 | 91 | 90 | 92 | 95 |
| AMPK | 61 | 48 | 86 | 84 | 91 | 80 | | | | | 30 | | | | | | |
| AMPK (hum) | 65 | 55 | 90 | 98 | 87 | 71 | 73 | 75 | 94 | 49 | 27 | 80 | 76 | 71 | 101 | 69 | 96 |
| MARK1 | 75 | 83 | 89 | 90 | 103 | 99 | | | | | 96 | | | | | | |
| MARK2 | 67 | 74 | 90 | 79 | 102 | 84 | | | | | 65 | | | | | | |
| MARK3 | 68 | 65 | 79 | 75 | 85 | 68 | 106 | 106 | 72 | 63 | 33 | 98 | 109 | 103 | 100 | 105 | 101 |
| MARK4 | 82 | 77 | 90 | 102 | 95 | 71 | | | | | 67 | | | | | | |
| BRSK1 | 56 | 45 | 63 | 70 | 83 | 95 | | | | | 43 | | | | | | |
| BRSK2 | 74 | 52 | 79 | 81 | 82 | 80 | | | | | 34 | | | | | | |
| MELK | 22 | 29 | 31 | 48 | 29 | 22 | | | | | 18 | | | | | | |
| NUAK1 | 57 | 39 | 52 | 86 | 68 | 64 | | | | | 14 | | | | | | |
| SIK2 | 82 | 68 | 77 | 79 | 69 | 96 | | | | | 26 | | | | | | |
| SIK3 | 67 | 80 | 82 | 99 | 92 | 96 | | | | | 42 | | | | | | |
| TSSK1 | 85 | 109 | 66 | 97 | 75 | 95 | | | | | 27 | | | | | | |
| CK1γ2 | 62 | 20 | 57 | 81 | 25 | 83 | | | | | 3 | | | | | | |
| CK2 | 50 | 19 | 57 | 68 | 88 | 78 | 80 | 78 | 88 | 75 | 16 | 12 | 90 | 89 | 97 | 86 | 46 |
| TTBK1 | 70 | 47 | 91 | 99 | 89 | 100 | | | | | 46 | | | | | | |
| TTBK2 | 74 | 51 | 102 | 99 | 102 | 71 | | | | | 44 | | | | | | |
| DYRK1A | 15 | 8 | 33 | 50 | 29 | 25 | 9 | 30 | 6 | 6 | 2 | 3 | 11 | 2 | 51 | 13 | 51 |
| NEK2a | 79 | 74 | 92 | 93 | 99 | 89 | | | | | 64 | | | | | | |
| NEK6 | 75 | 84 | 98 | 72 | 107 | 107 | 94 | 86 | 94 | 112 | 97 | 97 | 106 | 90 | 93 | 87 | 99 |
| IKKb | 82 | 63 | 84 | 80 | 81 | 88 | | | | | 87 | | | | | | |
| IKKe | 47 | 50 | 78 | 69 | 81 | 63 | | | | | 27 | | | | | | |
| TBK1 | 61 | 81 | 68 | 80 | 97 | 73 | 96 | 100 | 95 | 66 | 36 | 94 | 92 | 101 | 102 | 96 | 98 |
| PIM1 | 59 | 42 | 51 | 74 | 25 | 39 | 78 | 19 | 76 | 14 | 35 | 32 | 69 | 72 | 95 | 99 | 50 |
| PIM2 | 90 | 76 | 75 | 89 | 69 | 77 | | | | | 67 | | | | | | |
| SRPK1 | 19 | 16 | 63 | 66 | 58 | 57 | 61 | 42 | 10 | 10 | 3 | 7 | 19 | 54 | 68 | 55 | 82 |
| EF2K | 79 | 67 | 69 | 79 | 106 | 94 | 99 | 115 | 108 | 92 | 107 | 100 | 134 | 108 | 91 | 94 | 127 |
| EIF2AK3 | 59 | 51 | 73 | 65 | 87 | 89 | | | | | 45 | | | | | | |
| HIPK1 | 44 | 43 | 47 | 75 | 41 | 76 | | | | | 9 | | | | | | |
| HIPK2 | 23 | 19 | 18 | 67 | 52 | 43 | 90 | 74 | 41 | 36 | 8 | 62 | 78 | 72 | 87 | 66 | 96 |
| HIPK3 | 90 | 45 | 84 | 106 | 102 | 82 | | | | | 38 | | | | | | |
| PAK2 | 108 | 85 | 104 | 88 | 114 | 119 | | | | | 94 | | | | | | |
| PAK4 | 69 | 64 | 87 | 73 | 92 | 115 | 154 | 107 | 37 | 67 | 35 | 94 | 111 | 89 | 100 | 83 | 109 |
| PAK5 | 79 | 88 | 94 | 92 | 109 | 82 | | | | | 70 | | | | | | |
| PAK6 | 93 | 94 | 101 | 90 | 119 | 99 | | | | | 104 | | | | | | |
| MST2 | 55 | 57 | 61 | 84 | 73 | 60 | 93 | 95 | 86 | 46 | 40 | 103 | 110 | 99 | 77 | 88 | 119 |
| MST3 | 77 | 76 | 85 | 92 | 90 | 78 | | | | | 54 | | | | | | |
| MST4 | 79 | 80 | 80 | 134 | 103 | 76 | | | | | 71 | | | | | | |
| GCK | 27 | 31 | 29 | 33 | 25 | 39 | | | | | 4 | | | | | | |
| MAP4K3 | 48 | 56 | 54 | 73 | 69 | 67 | | | | | 56 | | | | | | |
| MAP4K5 | 67 | 81 | 74 | 92 | 58 | 50 | | | | | 31 | | | | | | |
| MINK1 | 37 | 19 | 48 | 63 | 51 | 31 | | | | | 7 | | | | | | |
| MEKK1 | 76 | 107 | 127 | 106 | 107 | 114 | | | | | 105 | | | | | | |
| MLK1 | 33 | 13 | 31 | 71 | 61 | 68 | | | | | 5 | | | | | | |
| MLK3 | 30 | 26 | 46 | 95 | 48 | 57 | 72 | 40 | 20 | 15 | 5 | 56 | 49 | 54 | 76 | 68 | 73 |
| TESK1 | 73 | 70 | 84 | 88 | 102 | 93 | | | | | 65 | | | | | | |
| TAO1 | 81 | 68 | 74 | 77 | 87 | 80 | | | | | 62 | | | | | | |
| ASK1 | 37 | 18 | 70 | 79 | 51 | 88 | | | | | 12 | | | | | | |
| TAK1 | 25 | 18 | 33 | 55 | 73 | 34 | 95 | 45 | 60 | 31 | 9 | 37 | 79 | 76 | 81 | 68 | 35 |
| IRAK1 | 38 | 37 | 37 | 68 | 57 | 38 | | | | | 26 | | | | | | |
| IRAK4 | 42 | 32 | 54 | 69 | 42 | 55 | 70 | 57 | 46 | 34 | 22 | 70 | 72 | 78 | 63 | 96 | 58 |
| RIPK2 | 30 | 21 | 29 | 60 | 20 | 27 | 89 | 40 | 34 | 24 | 12 | 78 | 69 | 79 | 39 | 48 | 99 |
| OSR1 | 72 | 51 | 59 | 90 | 109 | 97 | | | | | 82 | | | | | | |
| TTK | 32 | 22 | 36 | 74 | 45 | 53 | 32 | 71 | 18 | 30 | 19 | 42 | 47 | 9 | 94 | 35 | 95 |
| MPSK1 | 77 | 81 | 90 | 73 | 101 | 102 | | | | | 106 | | | | | | |
| WNK1 | 89 | 99 | 91 | 88 | 103 | 100 | | | | | 108 | | | | | | |
| ULK1 | 69 | 78 | 96 | 90 | 88 | 78 | | | | | 47 | | | | | | |
| ULK2 | 63 | 84 | 87 | 86 | 85 | 56 | | | | | 69 | | | | | | |

-continued

| Kinase | | | | | | | | | | | | | | | | | |
|---|---|---|---|---|---|---|---|---|---|---|---|---|---|---|---|---|---|
| TGFBR1 | 106 | 103 | 117 | 107 | 88 | 109 | | | | | 93 | | | | | | |
| Src | 62 | 72 | 105 | 79 | 75 | 70 | 87 | 77 | 172 | 30 | 33 | 85 | 74 | 165 | 169 | 178 | 79 |
| Lck | 79 | 82 | 82 | 93 | 105 | 77 | 92 | 93 | 93 | 98 | 92 | 95 | 102 | 99 | 100 | 93 | 111 |
| CSK | 89 | 83 | 101 | 94 | 88 | 95 | | | | | 69 | | | | | | |
| YES1 | 79 | 74 | 73 | 82 | 91 | 60 | | | | | 65 | | | | | | |
| ABL | 76 | 58 | 113 | 99 | 105 | 71 | | | | | 54 | | | | | | |
| BTK | 59 | 54 | 71 | 107 | 110 | 90 | 79 | 75 | 56 | 81 | 59 | 49 | 73 | 95 | 68 | 77 | 74 |
| JAK2 | 50 | 30 | 71 | 66 | 70 | 98 | 87 | 86 | 81 | 47 | 36 | 87 | 109 | 101 | 85 | 89 | 113 |
| SYK | 90 | 71 | 99 | 75 | 86 | 106 | 120 | 83 | 109 | 80 | 64 | 93 | 117 | 102 | 96 | 79 | 108 |
| ZAP70 | 92 | 79 | 91 | 89 | 110 | 105 | | | | | 109 | | | | | | |
| TIE2 | 80 | 81 | 76 | 84 | 100 | 106 | | | | | 41 | | | | | | |
| BRK | 43 | 21 | 61 | 93 | 46 | 94 | | | | | 14 | | | | | | |
| EPH-A2 | 77 | 81 | 85 | 84 | 108 | 81 | 110 | 91 | 95 | 65 | 77 | 89 | 98 | 100 | 76 | 84 | 96 |
| EPH-A4 | 92 | 89 | 78 | 91 | 92 | 89 | | | | | 87 | | | | | | |
| EPH-B1 | 93 | 93 | 94 | 99 | 104 | 98 | | | | | 98 | | | | | | |
| EPH-B2 | 99 | 91 | 103 | 89 | 99 | 72 | | | | | 78 | | | | | | |
| EPH-B3 | 88 | 65 | 63 | 76 | 108 | 44 | | | | | 93 | | | | | | |
| EPH-B4 | 92 | 100 | 84 | 97 | 106 | 88 | | | | | 110 | | | | | | |
| FGF-R1 | 54 | 56 | 16 | 74 | 102 | 81 | | | | | 84 | | | | | | |
| HER4 | 40 | 17 | 33 | 96 | 48 | 98 | 85 | 81 | 73 | 45 | 16 | 82 | 90 | 122 | 99 | 107 | 103 |
| IGF-1R | 88 | 54 | 54 | 107 | 50 | 84 | 85 | 100 | 104 | 52 | 18 | 131 | 88 | 101 | 123 | 96 | 104 |
| IR | 51 | 35 | 27 | 106 | 105 | 74 | | | | | 31 | | | | | | |
| IRR | 71 | 45 | 82 | 86 | 51 | 78 | | | | | 31 | | | | | | |
| TrkA | 81 | 71 | 49 | 87 | 51 | 57 | 84 | 35 | 60 | 38 | 23 | 66 | 74 | 82 | 85 | 111 | 87 |
| DDR2 | 89 | 93 | 104 | 115 | 109 | 85 | | | | | 112 | | | | | | |
| VEG-FR | 20 | 21 | 17 | 58 | 50 | 24 | 28 | 65 | 37 | 11 | 5 | 36 | 53 | 29 | 77 | 66 | 86 |
| PDGFRA | 40 | 44 | 56 | 63 | 61 | 43 | | | | | 29 | | | | | | |
| PINK | | | | | | | | | | | | | | | | | |

| Kinase | MS:LY-2-77 | 08-39 | MS:LY-2-89 | 03-58 | MS:LY-2-85 | MS:LY-2-87 | 03-74 | 03-80 |
|---|---|---|---|---|---|---|---|---|
| MKK1 | 95 | 106 | 56 | 52 | 83 | 69 | 35 | 80 |
| MKK2 | 95 | 78 | 47 | 86 | 80 | 73 | | 75 |
| MKK6 | 111 | 96 | 98 | 103 | 99 | 107 | | 115 |
| ERK1 | 87 | 18 | 54 | 84 | 86 | 70 | | 94 |
| ERK2 | 105 | 68 | 68 | 104 | 98 | 81 | | 101 |
| ERK5 | 74 | 47 | 32 | 31 | 45 | 54 | | 27 |
| JNK1 | 104 | 92 | 68 | 80 | 97 | 105 | 80 | 86 |
| JNK2 | 99 | 93 | 93 | 99 | 100 | 105 | | 87 |
| JNK3 | 88 | 53 | 36 | 51 | 62 | 66 | | 79 |
| p38a MAPK | 109 | 96 | 18 | 81 | 89 | 73 | 106 | 79 |
| p38b MAPK | 110 | 96 | 17 | 75 | 92 | 82 | | 77 |
| p38g MAPK | 121 | 90 | 64 | 64 | 80 | 93 | | 83 |
| p38d MAPK | 98 | 67 | 70 | 75 | 72 | 75 | | 102 |
| RSK1 | 85 | 30 | 13 | 35 | 54 | 29 | 19 | 90 |
| RSK2 | 81 | 2 | 8 | 51 | 32 | 28 | | 66 |
| PDK1 | 103 | 66 | 44 | 96 | 80 | 69 | 93 | 86 |
| PKBa | 89 | 84 | 82 | 92 | 90 | 86 | 87 | 105 |
| PKBb | 44 | 4 | 7 | 80 | 22 | 18 | | 93 |
| SGK1 | 101 | 35 | 28 | 41 | 75 | 43 | 59 | 55 |
| S6K1 | 94 | 12 | 14 | 9 | 50 | 39 | 29 | 97 |
| PKA | 102 | 88 | 87 | 90 | 98 | 93 | 90 | 104 |
| ROCK 2 | 96 | 22 | 11 | 10 | 29 | 38 | 32 | 80 |
| PRK2 | 92 | 42 | 44 | 36 | 66 | 67 | 54 | 79 |
| PKCa | 97 | 43 | 48 | 96 | 63 | 59 | 92 | 125 |
| PKCγ | 94 | 44 | 63 | 86 | 80 | 74 | | 87 |
| PKCz | 107 | 38 | 80 | 84 | 101 | 83 | | 75 |
| PKD1 | 114 | 32 | 22 | 54 | 49 | 52 | 53 | 82 |
| STK33 | 99 | 61 | 37 | 45 | 75 | 51 | | 60 |
| MSK1 | 107 | 56 | 46 | 46 | 69 | 66 | 63 | 70 |
| MNK1 | 85 | 66 | 27 | 33 | 40 | 19 | | 78 |
| MNK2 | 79 | 61 | 40 | 33 | 53 | 43 | | 75 |
| MAPKAP-K2 | 92 | 56 | 37 | 63 | 69 | 55 | | 71 |
| MAPKAP-K3 | 54 | 9 | 11 | 91 | 24 | 44 | | 76 |
| PRAK | 76 | 17 | 19 | 42 | 30 | 46 | | 75 |
| CAMKKb | 77 | 57 | 22 | 31 | 32 | 38 | 65 | 49 |
| CAMK1 | 60 | 8 | 43 | 30 | 62 | 65 | 35 | 50 |
| SmMLCK | 56 | 34 | 7 | 13 | 13 | 20 | 12 | 40 |
| PHK | 91 | 72 | 14 | 48 | 40 | 13 | | 42 |
| DAPK1 | 95 | 31 | 22 | 24 | 48 | 36 | | 63 |
| CHK1 | 107 | 83 | 81 | 79 | 134 | 81 | | 75 |
| CHK2 | 75 | 18 | 10 | 4 | 25 | 17 | 6 | 50 |

| | | | | | | | | |
|---|---|---|---|---|---|---|---|---|
| CDK2-Cyclin A | 95 | 75 | 45 | 85 | 106 | 79 | | 95 |
| CDK9-Cyclin T1 | 88 | 69 | 62 | 86 | 72 | 87 | | 6 |
| PLK1 | 109 | 83 | 61 | 69 | 75 | 68 | 82 | 77 |
| Aurora A | 114 | 97 | 40 | 96 | 103 | 71 | | 102 |
| TLK1 | 102 | 98 | 88 | 78 | 93 | 94 | | 105 |
| LKB1 | 99 | 46 | 28 | 60 | 76 | 104 | 80 | 86 |
| AMPK | 95 | 25 | 40 | 26 | 57 | 45 | | 82 |
| AMPK (hum) | 100 | 44 | 37 | 36 | 49 | 42 | 58 | 69 |
| MARK1 | 96 | 77 | 64 | 69 | 77 | 94 | | 58 |
| MARK2 | 109 | 56 | 27 | 87 | 73 | 50 | | 69 |
| MARK3 | 102 | 48 | 16 | 45 | 58 | 44 | 67 | 78 |
| MARK4 | 89 | 58 | 49 | 68 | 82 | 59 | | 75 |
| BRSK1 | 102 | 38 | 38 | 61 | 73 | 35 | | 63 |
| BRSK2 | 104 | 24 | 37 | 53 | 56 | 48 | | 62 |
| MELK | 59 | 29 | 8 | 13 | 11 | 11 | | 83 |
| NUAK1 | 52 | 3 | 12 | 37 | 32 | 23 | | 80 |
| SIK2 | 92 | 20 | 7 | 17 | 23 | 36 | | 94 |
| SIK3 | 94 | 40 | 28 | 57 | 77 | 63 | | 73 |
| TSSK1 | 77 | 39 | 27 | 25 | 35 | 64 | | 57 |
| CK1γ2 | 62 | 15 | 28 | 6 | 45 | 57 | | 38 |
| CK2 | 103 | 25 | 10 | 23 | 65 | 51 | 7 | 83 |
| TTBK1 | 103 | 86 | 84 | 60 | 112 | 68 | | 91 |
| TTBK2 | 105 | 67 | 73 | 45 | 89 | 73 | | 81 |
| DYRK1A | 55 | 16 | 4 | 4 | 7 | 11 | 4 | 2 |
| NEK2a | 109 | 13 | 64 | 65 | 105 | 76 | | 83 |
| NEK6 | 96 | 36 | 81 | 101 | 97 | 57 | 48 | 81 |
| IKKb | 104 | 54 | 57 | 89 | 72 | 71 | | 79 |
| IKKe | 79 | 14 | 24 | 44 | 51 | 34 | | 68 |
| TBK1 | 89 | 78 | 57 | 50 | 80 | 99 | 72 | 94 |
| PIM1 | 39 | 26 | 6 | 31 | 9 | 22 | 27 | 65 |
| PIM2 | 81 | 70 | 19 | 65 | 58 | 42 | | 99 |
| SRPK1 | 75 | 9 | 4 | 15 | 11 | 16 | 19 | 50 |
| EF2K | 111 | 68 | 59 | 103 | 70 | 77 | 95 | 88 |
| EIF2AK3 | 93 | 67 | 48 | 39 | 61 | 78 | | 93 |
| HIPK1 | 102 | 68 | 53 | 12 | 84 | 93 | | 46 |
| HIPK2 | 65 | 17 | 22 | 14 | 39 | 32 | 15 | 8 |
| HIPK3 | 107 | 36 | 39 | 48 | 78 | 67 | | 25 |
| PAK2 | 79 | 43 | 59 | 97 | 79 | 84 | | 95 |
| PAK4 | 94 | 66 | 35 | 52 | 51 | 113 | 47 | 74 |
| PAK5 | 101 | 67 | 57 | 80 | 68 | 120 | | 86 |
| PAK6 | 114 | 92 | 85 | 117 | 94 | 93 | | 96 |
| MST2 | 76 | 21 | 19 | 49 | 39 | 44 | 43 | 83 |
| MST3 | 93 | 73 | 55 | 78 | 87 | 68 | | 124 |
| MST4 | 85 | 23 | 33 | 60 | 60 | 60 | | 76 |
| GCK | 77 | 26 | 11 | 7 | 25 | 17 | | 71 |
| MAP4K3 | 103 | 44 | 10 | 14 | 39 | 33 | | 105 |
| MAP4K5 | 80 | 44 | 46 | 37 | 45 | 42 | | 86 |
| MINK1 | 48 | 7 | 3 | 14 | 8 | 5 | | 84 |
| MEKK1 | 113 | 82 | 103 | 109 | 109 | 90 | | 78 |
| MLK1 | 68 | 13 | 8 | 7 | 28 | 18 | | 71 |
| MLK3 | 91 | 22 | 18 | 7 | 42 | 32 | 6 | 59 |
| TESK1 | 85 | 69 | 82 | 83 | 74 | 85 | | 106 |
| TAO1 | 99 | 52 | 66 | 77 | 79 | 100 | | 87 |
| ASK1 | 96 | 70 | 46 | 29 | 57 | 49 | | 61 |
| TAK1 | 104 | 23 | 13 | 16 | 37 | 23 | 10 | 90 |
| IRAK1 | 78 | 33 | 22 | 29 | 36 | 32 | | 73 |
| IRAK4 | 83 | 39 | 26 | 33 | 50 | 47 | 21 | 66 |
| RIPK2 | 84 | 62 | 12 | 9 | 14 | 26 | 13 | 49 |
| OSR1 | 96 | 72 | 84 | 86 | 103 | 88 | | 95 |
| TTK | 56 | 25 | 20 | 36 | 31 | 40 | 14 | 56 |
| MPSK1 | 104 | 112 | 98 | 103 | 99 | 113 | | 97 |
| WNK1 | 92 | 86 | 110 | 115 | 111 | 111 | | 97 |
| ULK1 | 98 | 80 | 45 | 59 | 55 | 68 | | 80 |
| ULK2 | 115 | 77 | 33 | 61 | 68 | 67 | | 93 |
| TGFBR1 | 109 | 110 | 87 | 91 | 124 | 102 | | 83 |
| Src | 108 | 54 | 12 | 47 | 210 | 23 | 76 | 96 |
| Lck | 97 | 79 | 34 | 99 | 76 | 45 | 45 | 90 |
| CSK | 100 | 84 | 60 | 85 | 85 | 79 | | 95 |
| YES1 | 93 | 74 | 14 | 80 | 66 | 21 | | 88 |
| ABL | 108 | 85 | 32 | 64 | 87 | 45 | | 101 |
| BTK | 83 | 37 | 47 | 76 | 100 | 58 | 32 | 98 |
| JAK2 | 105 | 48 | 32 | 46 | 71 | 47 | 53 | 80 |
| SYK | 91 | 88 | 78 | 70 | 71 | 75 | 71 | 97 |
| ZAP70 | 83 | 103 | 90 | 105 | 118 | 128 | | 107 |
| TIE2 | 103 | 76 | 46 | 59 | 92 | 67 | | 91 |
| BRK | 90 | 59 | 45 | 22 | 63 | 79 | | 84 |

-continued

| | | | | | | | | |
|---|---|---|---|---|---|---|---|---|
| EPH-A2 | 94 | 54 | 63 | 97 | 81 | 69 | 73 | 90 |
| EPH-A4 | 86 | 104 | 49 | 99 | 105 | 86 | | 74 |
| EPH-B1 | 101 | 86 | 87 | 106 | 103 | 79 | | 103 |
| EPH-B2 | 124 | 108 | 53 | 89 | 130 | 67 | | 93 |
| EPH-B3 | 76 | 44 | 45 | 101 | 75 | 67 | | 124 |
| EPH-B4 | 83 | 107 | 74 | 100 | 113 | 92 | | 97 |
| FGF-R1 | 95 | 16 | 47 | 91 | 89 | 69 | | 98 |
| HER4 | 67 | 31 | 20 | 29 | 66 | 32 | 31 | 102 |
| IGF-1R | 96 | 46 | 61 | 32 | 92 | 80 | 33 | 71 |
| IR | 74 | 49 | 29 | 51 | 67 | 70 | | 91 |
| IRR | 89 | 66 | 68 | 28 | 70 | 70 | | 52 |
| TrkA | 75 | 56 | 45 | 36 | 73 | 44 | 56 | 97 |
| DDR2 | 112 | 88 | 62 | 104 | 94 | 76 | | 84 |
| VEG-FR | 90 | 8 | 12 | 7 | 47 | 17 | 11 | 19 |
| PDGFRA | 90 | 44 | 28 | 32 | 47 | 43 | | 38 |
| PINK | | | | | | | | 112 |

Results for Compounds of Example 3

| Kinase | 03-07 | 03-17 | 13-03 |
|---|---|---|---|
| MKK1 | 85 | 106 | 70 |
| MKK2 | 88 | 50 | |
| MKK6 | 114 | 106 | |
| ERK1 | 102 | 115 | |
| ERK2 | 96 | 103 | |
| ERK5 | 48 | 79 | |
| JNK1 | 103 | 103 | 88 |
| JNK2 | 104 | 87 | |
| JNK3 | 50 | 86 | |
| p38a MAPK | 93 | 100 | 103 |
| p38b MAPK | 96 | 81 | |
| p38g MAPK | 93 | 95 | |
| p38d MAPK | 81 | 97 | |
| RSK1 | 48 | 93 | 77 |
| RSK2 | 71 | 105 | |
| PDK1 | 72 | 104 | 113 |
| PKBa | 103 | 96 | 106 |
| PKBb | 26 | 114 | |
| SGK1 | 64 | 215 | 91 |
| S6K1 | 26 | 92 | 90 |
| PKA | 91 | 98 | 97 |
| ROCK 2 | 27 | 83 | 70 |
| PRK2 | 74 | 89 | 105 |
| PKCa | 81 | 87 | 119 |
| PKCγ | 98 | 116 | |
| PKCz | 107 | 108 | |
| PKD1 | 61 | 102 | 113 |
| STK33 | 63 | 85 | |
| MSK1 | 62 | 101 | 97 |
| MNK1 | 40 | 103 | |
| MNK2 | 50 | 85 | |
| MAPKAP-K2 | 51 | 95 | |
| MAPKAP-K3 | 34 | 76 | |
| PRAK | 59 | 79 | |
| CAMKKb | 30 | 103 | 91 |
| CAMK1 | 44 | 90 | 94 |
| SmMLCK | 21 | 63 | 85 |
| PHK | 55 | 106 | |
| DAPK1 | 28 | 85 | |
| CHK1 | 113 | 86 | |
| CHK2 | 23 | 83 | 92 |
| CDK2-Cyclin A | 99 | 94 | |
| CDK9-Cyclin T1 | 76 | 80 | |
| PLK1 | 93 | 94 | 93 |
| Aurora A | 110 | 112 | |
| TLK1 | 108 | 103 | |
| LKB1 | 83 | 96 | 110 |
| AMPK | 76 | 86 | |
| AMPK (hum) | 34 | 100 | 99 |
| MARK1 | 106 | 108 | |
| MARK2 | 73 | 90 | |
| MARK3 | 72 | 86 | 92 |
| MARK4 | 71 | 94 | |
| BRSK1 | 52 | 109 | |
| BRSK2 | 66 | 102 | |

-continued

| Kinase | 03-07 | 03-17 | 13-03 |
|---|---|---|---|
| MELK | 12 | 79 | |
| NUAK1 | 37 | 85 | |
| SIK2 | 28 | 68 | |
| SIK3 | 56 | 75 | |
| TSSK1 | 57 | 98 | |
| CK1γ2 | 77 | 82 | |
| CK2 | 35 | 50 | 97 |
| TTBK1 | 93 | 92 | |
| TTBK2 | 71 | 108 | |
| DYRK1A | 30 | 45 | 45 |
| NEK2a | 38 | 85 | |
| NEK6 | 91 | 95 | 107 |
| IKKb | 88 | 90 | |
| IKKe | 73 | 94 | |
| TBK1 | 92 | 82 | 98 |
| PIM1 | 25 | 74 | 96 |
| PIM2 | 61 | 82 | |
| SRPK1 | 27 | 84 | 86 |
| EF2K | 91 | 98 | 110 |
| EIF2AK3 | 69 | 88 | |
| HIPK1 | 90 | 95 | |
| HIPK2 | 46 | 73 | 96 |
| HIPK3 | 81 | 105 | |
| PAK2 | 90 | 103 | |
| PAK4 | 92 | 92 | 58 |
| PAK5 | 82 | 77 | |
| PAK6 | 106 | 92 | |
| MST2 | 68 | 98 | 107 |
| MST3 | 85 | 91 | |
| MST4 | 76 | 105 | |
| GCK | 35 | 84 | |
| MAP4K3 | 63 | 88 | |
| MAP4K5 | 56 | 85 | |
| MINK1 | 18 | 84 | |
| MEKK1 | 115 | 120 | |
| MLK1 | 26 | 99 | |
| MLK3 | 39 | 80 | 89 |
| TESK1 | 101 | 83 | |
| TAO1 | 84 | 113 | |
| ASK1 | 86 | 94 | |
| TAK1 | 53 | 69 | 96 |
| IRAK1 | 49 | 98 | |
| IRAK4 | 74 | 126 | 93 |
| RIPK2 | 18 | 96 | 76 |
| OSR1 | 87 | 97 | |
| TTK | 28 | 91 | 108 |
| MPSK1 | 108 | 88 | |
| WNK1 | 115 | 97 | |
| ULK1 | 70 | 85 | |
| ULK2 | 81 | 121 | |
| TGFBR1 | 113 | 121 | |
| Src | 101 | 102 | 100 |
| Lck | 88 | 88 | 89 |
| CSK | 105 | 93 | |
| YES1 | 49 | 104 | |
| ABL | 105 | 103 | |

-continued

| Kinase | 03-07 | 03-17 | 13-03 |
|---|---|---|---|
| BTK | 32 | 95 | 31 |
| JAK2 | 56 | 90 | 93 |
| SYK | 102 | 82 | 37 |
| ZAP70 | 94 | 196 | |
| TIE2 | 78 | 100 | |
| BRK | 80 | 137 | |
| EPH-A2 | 88 | 90 | 63 |
| EPH-A4 | 95 | 119 | |
| EPH-B1 | 104 | 105 | |
| EPH-B2 | 110 | 96 | |
| EPH-B3 | 64 | 98 | |
| EPH-B4 | 100 | 137 | |
| FGF-R1 | 66 | 80 | |
| HER4 | 50 | 109 | 130 |
| IGF-1R | 96 | 118 | 104 |
| IR | 66 | 86 | |
| IRR | 75 | 84 | |
| TrkA | 59 | 94 | 55 |
| DDR2 | 90 | 109 | |
| VEG-FR | 28 | 114 | 87 |
| PDGFRA | 44 | 65 | |

Results for Compound of Example 4

| Kinase | 13-62 |
|---|---|
| MKK1 | 15 |
| JNK1 | 114 |
| p38a MAPK | 21 |
| RSK1 | 25 |
| PDK1 | 77 |
| PKBa | 66 |
| SGK1 | 21 |
| S6K1 | 22 |
| PKA | 104 |
| ROCK 2 | 11 |
| PRK2 | 40 |
| PKCa | 102 |
| PKD1 | 41 |
| MSK1 | 41 |
| CAMKKb | 25 |
| CAMK1 | 8 |
| SmMLCK | 5 |
| CHK2 | 18 |
| PLK1 | 98 |
| LKB1 | 91 |
| AMPK (hum) | 23 |
| MARK3 | 12 |
| CK2 | 24 |
| DYRK1A | 7 |
| NEK6 | 104 |
| TBK1 | 48 |
| PIM1 | 14 |
| SRPK1 | 3 |
| EF2K | 85 |
| HIPK2 | 23 |
| PAK4 | 22 |
| MST2 | 3 |
| MLK3 | 13 |
| TAK1 | 11 |
| IRAK4 | 17 |
| RIPK2 | 6 |
| TTK | 25 |
| Src | 7 |
| Lck | 11 |
| BTK | 25 |
| JAK2 | 31 |
| SYK | 59 |
| EPH-A2 | 81 |

-continued

| Kinase | 13-62 |
|---|---|
| HER4 | 13 |
| IGF-1R | 62 |
| TrkA | 9 |
| VEG-FR | 7 |

2. Determination of IC50 Values for Selected Inhibitors from Example 1 Against DYRK1a IC 50 values were determined by measuring the inhibition of DYRK1a caused by each compound at a compound concentration of 100 µM, 30 µM, 10 µM, 3 µM, 1 µM, 0.3 µM, 0.1 µM, 0.03 µM, 0.01 µM and 0.003 µM. The kinase assay was carried out using Multidrop 384's at room temperature in a total assay volume of 25.5 µl. To plates containing 0.5 µl of compounds, DMSO controls or acid blanks, 15 µl of an enzyme mix containing the DYRK1a enzyme and peptide/protein substrate in buffer was added. Compounds were pre-incubated in the presence of the enzyme and peptide/protein substrate for 5 minutes before initiation of the reaction by addition of 10 µl of ATP (final concentration selected for each kinase at 5, 20 or 50 µM). Assays were carried out for 30 minutes at room temperature before termination by the addition of 5 µl orthophosphoric acid. The assay plates were then harvested onto P81 Unifilter Plates by a Packard Harvester (wash buffer is 50 mM orthophosphoric acid) and dried in air. The dry Unifilter plates were then sealed by the addition of MicroScint O and counted in Packard Topcount NXT scintillation counters. The measurements were performed in duplicate and the average determined and reported as the IC50 value and presented in the table below.

TABLE

Determined IC50 values (in µM) for inhibitors against DYRK1a.

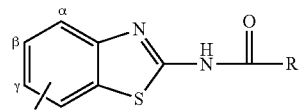

R = CH$_3$

| X | Compound | IC 50 (µM) |
|---|---|---|
| γ-OH | 01-71 | 28.1 |
| β-OH | 01-66 | 0.8 |
| γ-OCH$_3$ | 03-20 | 12.3 |
| β-OCH$_3$ | 03-21 | 0.4 |
| γ-F | 03-94 | 23.6 |
| β-F | 03-77 | 3.9 |
| γ-CF$_3$ | 01-90 | 1.1 |
| β-CF$_3$ | 03-73 | 26.5 |
| γ-CN | 01-94 | 1.3 |
| γ-NO$_2$ | 13-10 | 0.7 |
| γ-CONH$_2$ | 08-70 | 15.7 |

The invention claimed is:

1. A method of treating Alzheimer's disease or Parkinson's disease in a subject comprising administering a therapeutically effective amount of a compound of formula (I)

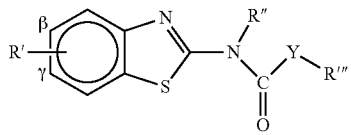

(I)

wherein:
  Y represents a C or N atom which may be substituted by $C_1$ alkyl or forms a cyclic group with R''' consisting of no more than 13 non-hydrogen atoms but may not be a quaternary C atom;
  R' is —$OR_1$, F, —OH, or —$OCOR_1$ in which $R_1$ is $C_{1-3}$ alkyl and is in the beta position;
  R'' is $C_{1-3}$ alkyl or H; and
  R''' is H or a group consisting of 1-12 non-hydrogen atoms
    wherein the group consisting of 1-12 non-hydrogen atoms is selected from —$CONH_2$, —$CH_2COCH_3$, —$CH_2CHNH_2CH_3$, —$NHCOCH_3$, —$CH_2CH_3$, —$CH_2CH_2CH_3$, —$COCH_3$, —$COCH_2CH_3$, or —$CONHCH_3$; or cyclohexyl, pyridine, pyrimidine, pyrazole, imidazole, thiazole, oxazole, diazolone, morpholine or piperidine, each of which is optionally substituted by —OH, —OR, —NRR, —C=O—OR, —C=O—NRR, —$SO_2$—NRR, —NR—$SO_2$R, —$SO_2$R, —NR—C=OR or a halogen, wherein each R may be the same or different and is H or $C_{1-3}$ alkyl; or
  wherein Y and R''' together form a cyclic group selected from cyclohexyl, phenyl, pyridine, pyrimidine, pyrazole, imidazole, thiazole, oxazole, diazolone, morpholine or piperidine, each of which is optionally substituted by —OH, —OR, —NRR, —C=O—OR, —C=O—NRR, —$SO_2$—NRR, —NR—$SO_2$R, —$SO_2$R, —NR—C=OR or a halogen, wherein each R may be the same or different and is H or $C_{1-3}$ alkyl;
or a salt, hydrate or solvate of a compound of formula (I), wherein the therapeutically effective amount is such as to inhibit formation of neurofibrillary (tau) tangles.

2. The method of claim 1 wherein Y represents a C atom and forms a cyclic group with R'''.

3. The method of claim 1 wherein R''' is hydrogen.

4. The method of claim 1 wherein Y is —$CH_2$— or —NH—.

5. The method of claim 1 wherein R'' is H or methyl.

6. The method of claim 1 wherein the Alzheimer's disease is in a subject with Downs Syndrome.

7. An in vitro method of inhibiting Dyrk1A or a reaction catalysed by Dyrk1A, the method comprising contacting said kinase with a compound of formula (I)

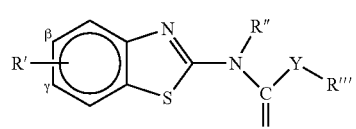

(I)

wherein:
  Y represents a C or N atom which may be substituted by $C_1$ alkyl or forms a cyclic group with R''' consisting of no more than 13 non-hydrogen atoms but may not be a quaternary C atom;
  R' is —$OR_1$, F, —OH, or —$OCOR_1$ in which $R_1$ is $C_{1-3}$ alkyl and is in the beta position;
  R'' is $C_{1-3}$ alkyl or H; and
  R''' is H or a group consisting of 1-12 non-hydrogen atoms;
    wherein the group consisting of 1-12 non-hydrogen atoms is selected from —$CONH_2$, —$CH_2COCH_3$, —$CH_2CHNH_2CH_3$, —$NHCOCH_3$, —$CH_2CH_3$, —$CH_2CH_2CH_3$, —$COCH_3$, —$COCH_2CH_3$, or —$CONHCH_3$; or cyclohexyl, pyridine, pyrimidine, pyrazole, imidazole, thiazole, oxazole, diazolone, morpholine or piperidine, each of which is optionally substituted by —OH, —OR, —NRR, —C=O—OR, —C=O—NRR, —$SO_2$—NRR, —NR—$SO_2$R, —$SO_2$R, —NR—C=OR or a halogen, wherein each R may be the same or different and is H or $C_{1-3}$ alkyl; or
  wherein Y and R''' together form a cyclic group selected from cyclohexyl, phenyl, pyridine, pyrimidine, pyrazole, imidazole, thiazole, oxazole, diazolone, morpholine or piperidine, each of which is optionally substituted by —OH, —OR, —NRR, —C=O—OR, —C=O—NRR, —$SO_2$—NRR, —NR—$SO_2$R, —$SO_2$R, —NR—C=OR or a halogen, wherein each R may be the same or different and is H or $C_{1-3}$ alkyl;
or a salt, hydrate or solvate of a compound of formula (I).

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Woodtide peptide

<400> SEQUENCE: 1

Lys Lys Ile Ser Gly Arg Leu Ser Pro Ile Met Thr Glu Gln
 1               5                  10